US011179377B2

(12) United States Patent
Straub et al.

(10) Patent No.: US 11,179,377 B2
(45) Date of Patent: Nov. 23, 2021

(54) PHARMACEUTICAL COMPOSITIONS AND USES THEREOF

(71) Applicant: Embera NeuroTherapeutics, Inc., Sudbury, MA (US)

(72) Inventors: Julie Straub, Winchester, MA (US); Muralikrishna Duvvuri, Chapel Hill, NC (US); Parag M. Ved, Lutz, FL (US); Bruce Rehlaender, Lake Oswego, OR (US); Jay Breaux, Chapel Hill, NC (US); Winston A. Vadino, Whitehouse Station, NJ (US); Kripanath Borah, Stewartsville, NJ (US); Carol Gloff, Natick, MA (US)

(73) Assignee: Embera NeuroTherapeutics, Inc., Sudbury, MA (US)

( * ) Notice: Subject to any disclaimer, the term of this patent is extended or adjusted under 35 U.S.C. 154(b) by 156 days.

(21) Appl. No.: 16/492,804

(22) PCT Filed: Mar. 12, 2018

(86) PCT No.: PCT/US2018/021939
§ 371 (c)(1),
(2) Date: Sep. 10, 2019

(87) PCT Pub. No.: WO2018/165649
PCT Pub. Date: Sep. 13, 2018

(65) Prior Publication Data
US 2020/0054615 A1 Feb. 20, 2020

Related U.S. Application Data

(60) Provisional application No. 62/469,798, filed on Mar. 10, 2017.

(51) Int. Cl.
| A61K 31/444 | (2006.01) |
| A61K 9/24 | (2006.01) |
| A61K 9/28 | (2006.01) |
| A61K 9/48 | (2006.01) |
| A61K 31/5513 | (2006.01) |

(52) U.S. Cl.
CPC .......... *A61K 31/444* (2013.01); *A61K 9/209* (2013.01); *A61K 9/28* (2013.01); *A61K 9/4808* (2013.01); *A61K 31/5513* (2013.01)

(58) Field of Classification Search
CPC ........ A61K 31/444; A61K 9/209; A61K 9/28; A61K 9/4808; A61K 31/5513
See application file for complete search history.

(56) References Cited

U.S. PATENT DOCUMENTS

| 4,594,329 A | 6/1986 | Vale, Jr. |
| 4,605,642 A | 8/1986 | Rivier |
| 4,661,493 A | 4/1987 | Gibbs |
| 4,814,333 A | 3/1989 | Ravaris |
| 4,816,567 A | 3/1989 | Cabilly et al. |
| 4,925,844 A | 5/1990 | Resch |
| 4,942,162 A | 7/1990 | Rosenberg |
| 5,006,528 A | 4/1991 | Oshiro et al. |
| 5,008,528 A | 4/1991 | Duchon |
| 5,016,655 A | 5/1991 | Waddell |
| 5,456,850 A | 10/1995 | Trabitzsch |
| 5,869,474 A | 2/1999 | Goeders |
| 6,323,312 B1 | 11/2001 | Rivier |
| 6,326,463 B1 | 12/2001 | Rivier |
| 7,612,088 B2 | 11/2009 | Herold et al. |
| 8,030,334 B2 | 10/2011 | Adams et al. |
| 8,153,674 B2 | 4/2012 | Adams et al. |
| 8,263,125 B2 | 9/2012 | Vaya et al. |
| 8,314,097 B2 | 11/2012 | Ksander et al. |
| 8,383,827 B2 | 2/2013 | Chamoin et al. |
| 8,436,035 B2 | 5/2013 | Adams et al. |
| 8,455,522 B2 | 6/2013 | Hu et al. |
| 8,519,134 B2 | 8/2013 | Allan et al. |
| 8,519,142 B2 | 8/2013 | Chamoin et al. |

(Continued)

FOREIGN PATENT DOCUMENTS

| CN | 104288385 A | 1/2015 |
| EP | 0125023 A1 | 11/1984 |

(Continued)

OTHER PUBLICATIONS

Sonino, The use of ketoconazole as an inhibitor of steroid production. N Engl J Med. Sep. 24, 1987;317(13):812-8.
Stewart, Pathways to relapse: the neurobiology of drug- and stress-induced relapse to drug-taking. J Psychiatry Neurosci. Mar. 2000;25(2):125-36.
Strohle et al., Stress responsive neurohormones in depression and anxiety. Pharmacopsychiatry. Nov. 2003;36 Suppl 3:S207-14.
Tanaka et al., Sequence-specific interaction of alpha-beta-anomeric double-stranded DNA with the p50 subunit of NF kappa B: application to the decoy approach. Nucleic Acids Res. Aug. 11, 1994;22(15):3069-74.
Tarr et al., Cocaine. Chemical Dependency. Apr. 1987;34(2):319-331.

(Continued)

Primary Examiner — Robert A Wax
Assistant Examiner — Olga V. Tcherkasskaya
(74) Attorney, Agent, or Firm — McCarter & English, LLP; Jonathan M. Sparks; Michael J. DeGrazia

(57) ABSTRACT

Provided are pharmaceutical compositions useful for the treatment and/or prevention of a disorder, such as addiction. For example, pharmaceutical compositions are provided that comprise a first active pharmaceutical component (e.g., metyrapone) and a second active pharmaceutical component (e.g., oxazepam). The compositions may be constructed in such a manner as to limit the physical contact between the first and second active pharmaceutical components, thus preventing any degradation of the active pharmaceutical components resulting form interaction between the two components. The compositions may include at least one pharmaceutically acceptable excipient. Also provided are methods of making the compositions as well as kits containing materials to provide the compositions.

8 Claims, No Drawings

(56) References Cited

U.S. PATENT DOCUMENTS

| | | |
|---|---|---|
| 8,541,404 B2 | 9/2013 | Hartmann et al. |
| 8,575,160 B2 | 11/2013 | Sun et al. |
| 8,609,862 B2 | 12/2013 | Hu et al. |
| 8,680,079 B2 | 3/2014 | Herold et al. |
| 8,685,960 B2 | 4/2014 | Hartmann et al. |
| 8,940,315 B2 | 1/2015 | Hobot et al. |
| 9,078,886 B2 | 7/2015 | Goeders |
| 9,415,107 B2 | 8/2016 | Goeders |
| 9,987,286 B2 | 6/2018 | Goeders et al. |
| 2002/0078969 A1 | 6/2002 | Wastchak et al. |
| 2003/0211157 A1 | 11/2003 | Simon |
| 2004/0092481 A1 | 5/2004 | Jerussi |
| 2004/0185170 A1 | 9/2004 | Chungi et al. |
| 2004/0204401 A1 | 10/2004 | Migaly |
| 2005/0037983 A1 | 2/2005 | Dinan |
| 2005/0058705 A1 | 3/2005 | Remon et al. |
| 2005/0090553 A1 | 4/2005 | Shapiro |
| 2005/0203130 A1 | 9/2005 | Buntinx |
| 2005/0215533 A1 | 9/2005 | Gottlieb |
| 2008/0152709 A1 | 6/2008 | Bortz |
| 2008/0206138 A1 | 8/2008 | Zolle et al. |
| 2009/0203669 A1 | 8/2009 | Goeders |
| 2010/0112056 A1 | 5/2010 | Rourke et al. |
| 2012/0071512 A1 | 3/2012 | Hu et al. |
| 2012/0208795 A1 | 8/2012 | Goeders |
| 2012/0237482 A1 | 9/2012 | Rodriguez |
| 2012/0277215 A1 | 11/2012 | Ksander et al. |
| 2013/0045979 A1 | 2/2013 | Sanfilippo |
| 2013/0287789 A1 | 10/2013 | Ksander et al. |
| 2013/0296309 A1 | 11/2013 | Chamoin et al. |
| 2016/0346261 A1 | 12/2016 | Goeders |
| 2017/0051007 A1 | 2/2017 | Altschul et al. |
| 2018/0185375 A1 | 7/2018 | Detke et al. |
| 2019/0275058 A1 | 9/2019 | Detke et al. |
| 2019/0282583 A1 | 9/2019 | Detke et al. |
| 2020/0016134 A1 | 1/2020 | Detke et al. |
| 2020/0360400 A1 | 11/2020 | Detke |

FOREIGN PATENT DOCUMENTS

| | | |
|---|---|---|
| EP | 0171496 A2 | 2/1986 |
| EP | 0173494 A2 | 3/1986 |
| EP | 0184187 A2 | 6/1986 |
| EP | 393942 A1 | 10/1990 |
| EP | 1082960 A2 | 3/2001 |
| EP | 1666468 A1 | 6/2006 |
| JP | 2005-519850 A | 7/2005 |
| JP | 2009-515899 A | 4/2009 |
| WO | 1986/01533 A1 | 3/1986 |
| WO | 1988/09810 A1 | 12/1988 |
| WO | 1989/10134 A1 | 11/1989 |
| WO | 1991/00906 A1 | 1/1991 |
| WO | 1991/10741 A1 | 7/1991 |
| WO | 1992/03917 A1 | 3/1992 |
| WO | 1992/03918 A1 | 3/1992 |
| WO | 2000/54766 A1 | 9/2000 |
| WO | 2001/52833 A1 | 7/2001 |
| WO | 2004/009073 A1 | 1/2004 |
| WO | 2004/032916 A1 | 4/2004 |
| WO | 2005/026126 A1 | 3/2005 |
| WO | 2005/061508 A1 | 7/2005 |
| WO | 2005/100992 A1 | 10/2005 |
| WO | 2005/118557 A2 | 12/2005 |
| WO | 2005/118581 A1 | 12/2005 |
| WO | 2007/024945 A1 | 3/2007 |
| WO | 2007/056618 A1 | 5/2007 |
| WO | 2007/100775 A2 | 9/2007 |
| WO | 2007/117982 A2 | 10/2007 |
| WO | 2008/076336 A2 | 6/2008 |
| WO | 2009/135651 A1 | 11/2009 |
| WO | 2009/156462 A2 | 12/2009 |
| WO | 2010/130773 A2 | 11/2010 |
| WO | 2010/130794 A1 | 11/2010 |
| WO | 2010/130796 A1 | 11/2010 |
| WO | 2011/061168 A1 | 5/2011 |
| WO | 2011/064376 A1 | 6/2011 |
| WO | 2011/064769 A1 | 6/2011 |
| WO | 2011/088188 A1 | 7/2011 |
| WO | 2011/159871 A2 | 12/2011 |
| WO | 2013/160315 A2 | 10/2013 |
| WO | 2014/131825 A1 | 9/2014 |
| WO | 2014/210544 A2 | 12/2014 |
| WO | 2015/066344 A1 | 5/2015 |
| WO | 2016/209929 A1 | 12/2016 |
| WO | 2017/143034 A1 | 8/2017 |

OTHER PUBLICATIONS

Tasker, Endogenous cannabinoids take the edge off neuroendocrine responses to stress. Endocrinology. Dec. 2004;145(12):5429-30.

Thienpont et al., Ketoconazole—a new broad spectrum orally active antimycotic. Experientia. May 15, 1979;35(5):606-7.

Thomas et al., Comparative receptor binding analyses of cannabinoid agonists and antagonists. J Pharmacol Exp Ther. Apr. 1998;285(1):285-92.

Toulme, New candidates for true antisense. Nat Biotechnol. Jan. 2001;19(1):17-8.

Wolkowitz et al., Ketoconazole administration in hypercortisolemic depression. Am J Psychiatry. May 1993;150(5):810-2.

Wright et al., Attenuating corticosterone levels on the day of memory assessment prevents chronic stress-induced impairments in spatial memory. Eur J Neurosci. Jul. 2006;24(2):595-605.

Ye et al., Effects of ACTH, dexamethasone, and adrenalectomy on 11beta-hydroxylase (CYP11B1) and aldosterone synthase (CYP11B2) gene expression in the rat central nervous system. J Endocrinol. Feb. 2008;196(2):305-11.

Zhang et al., Interactions of corticotropin-releasing factor with antidepressant and anxiolytic drugs: behavioral studies with pigeons. Biol Psychiatry. May 1, 1990;27(9):953-67.

Zorrilla et al., Corticotropin releasing factor: a key role in the neurobiology of addiction. Front Neuroendocrinol. Apr. 2014;35(2):234-44.

International Search Report and Written Opinion for Application No. PCT/US2018/021939, dated May 23, 2018, 9 pages.

Akilandeswari et al., Efficacy of Antibacterial Activity of Antibiotics Ciprofloxacin and Gentamycin Improved with Anti Depressant Drug, Escitalopram. Int J Pharm Sci Rev Res. Jul.-Aug. 2013;21(2):71-4.

Arvat et al., The inhibitory effect of alprazolam, a benzodiazepine, overrides the stimulatory effect of metyrapone-induced lack of negative cortisol feedback on corticotroph secretion in humans. J Clin Endocrinol Metab. Aug. 1999;84(8):2611-5.

Azizi et al., Aldosterone synthase inhibition in humans. Nephrol Dial Transplant. Jan. 2013;28(1):36-43.

Baldessarini, Drugs and the Treatment of Psychiatric Disorders, Psychosis and Anxiety. Goodman & Gilman's The Pharmacological Basis of Therapeutics, Ninth Edition. McGraw-Hill, New York. Chapter 18, pp. 399-430, (1996).

Baumann et al., Effects of intravenous cocaine on plasma cortisol and prolactin in human cocaine abusers. Biol Psychiatry. Dec. 1, 1995;38(11):1751-5.

Bech et al., A case of sequential anti-stress medication in a patient with major depression resistant to amine-reuptake inhibitors. Acta Psychiatr Scand. Jul. 1999;100(1):76-8.

Bertagna et al., LCI699, a potent 11ß-hydroxylase inhibitor, normalizes urinary cortisol in patients with Cushing's disease: results from a multicenter, proof-of-concept study. J Clin Endocrinol Metab. Apr. 2014;99(4):1375-83.

Bourke et al., SSRI or CRF antagonism partially ameliorate depressive-like behavior after adolescent social defeat. Behav Brain Res. Aug. 15, 2014;270:295-9.

Brown et al., Ketoconazole Inhibits Chlordiazepoxide (COX) Clearance in Man; Differences in Acute and Chronic Treatment. Hepatology. 1984;4(5):1036, Abstract No. 117.

Chesley et al., Cocaine augments peripheral benzodiazepine binding in humans. J Clin Psychiatry. Oct. 1990;51(10):404-6.

Chouinard et al., Potentiation of fluoxetine by aminoglutethimide, an adrenal steroid suppressant, in obsessive-compulsive disorder

(56) References Cited

OTHER PUBLICATIONS resistant to SSRIs: a case report. Prog Neuropsychopharmacol Biol Psychiatry. Aug. 1996;20(6):1067-79.
Contoreggi et al., Stress hormone responses to corticotropin-releasing hormone in substance abusers without severe comorbid psychiatric disease. Biol Psychiatry. Nov. 1, 2003;54(9):873-8.
Crowley, Clinical Issues in Cocaine Abuse. Cocaine: Clinical and Biobehavioral Aspects. Seymour Fisher (Ed.). Oxford University Press, New York. Chapter 7, pp. 193-211 (1987).
De Lind Van Wijngaarden et al., High prevalence of central adrenal insufficiency in patients with Prader-Willi syndrome. J Clin Endocrinol Metab. May 2008;93(5):1649-54.
De Souza et al., Neuroendocrine effects of benzodiazepines. J Psychiatr Res. 1990;24 Suppl 2:111-9.
De Wit, Priming Effects With Drugs and Other Reinforcers. Experimental and Clinical Psychopharmacology. 1996;4(1):5-10.
Di Paolo et al., Endocrine and neurochemical actions of cocaine. Can J Physiol Pharmacol. Sep. 1989;67(9):1177-81.
Drouet et al., Metyrapone blunts stress-induced hyperthermia and increased locomotor activity independently of glucocorticoids and neurosteroids. Psychoneuroendocrinology. Oct. 2010;35(9):1299-310.
Elman et al., Acute cortisol administration triggers craving in individuals with cocaine dependence. Psychopharmacol Bull. 2003 Summer;37(3):84-9.
Engelhardt et al., Ketoconazole blocks cortisol secretion in man by inhibition of adrenal 11 beta-hydroxylase. Klin Wochenschr. Jul. 1, 1985;63(13):607-12.
Espallergues et al., The antidepressant-like effects of the 3beta-hydroxysteroid dehydrogenase inhibitor trilostane in mice is related to changes in neuroactive steroid and monoamine levels. Neuropharmacology. Jan. 2012;62(1):492-502.
Faria et al., Phosphoramidate oligonucleotides as potent antisense molecules in cells and in vivo. Nat Biotechnol. Jan. 2001;19(1);40-4.
Freel et al., Endogenous corticosteroid biosynthesis in subjects after bilateral adrenalectomy. Clin Endocrinol (Oxf). May 2007;66(5):659-65.
Gautier et al., Alpha-DNA. IV: Alpha-anomeric and beta-anomeric tetrathymidylates covalently linked to intercalating oxazolopyridocarbazole. Synthesis, physicochemical properties and poly (rA) binding. Nucleic Acids Res. Aug. 25, 1987;15(16):6625-41.
Gawin et al., Cocaine dependence. Annu Rev Med. 1989;40:149-61.
Gay, You've come a long way, baby! Coke time for the new American lady of the Eighties. J Psychoactive Drugs. Oct.-Dec. 1981;13(4):297-318.
Ghadirian et al., The psychotropic effects of inhibitors of steroid biosynthesis in depressed patients refractory to treatment. Biol Psychiatry. Mar. 15, 1995;37(6):369-75.
Goeders et al., Discovery and development of EMB-001 for the treatment of substance abuse disorders. Biological Psychiatry. May 1, 2015;77(9) Suppl. S, p. 136S. Abstiact No. 348.
Goeders et al., Effects of Ketoconazole on Intravenous Cocaine Self-Adminislialion in Rats. Problems of Drug Dependence 1996; Proceedings of the 58th Annual Scientific Meeting. National Institute on Drug Abuse Research, Monograph Series. 1996;174;180.
Goeders et al., Effects of oxazepam on methamphetamine-induced conditioned place preference. Pharmacol Biochem Behav. May 2004;78(1):185-8.
Goeders et al., Effects of surgical and pharmacological adrenalectomy on the initiation and maintenance of intravenous cocaine self-administration in rats. Brain Res. May 25, 1996;722(1-2):145-52.
Goeders et al., Effects of the combination of metyrapone and oxazepam on cocaine and food self-adminisliation in rats. Pharmacol Biochem Behav. Nov. 2008;91(1):181-9.
Goeders et al., Effects of the combination of metyrapone and oxazepam on intravenous nicotine self-adminislialion in rats. Psychopharmacology (Berl). Sep. 2012;223(1):17-25.

Goeders et al., Effects of the CRH receptor antagonist CP-154,526 on intravenous cocaine self-administration in rats. Neuropsychopharmacology. Nov. 2000;23(5):577-86.
Goeders et al., Ketoconazole reduces low dose cocaine self-adminislialion in rats. Drug Alcohol Depend. Dec. 1, 1998;53(1):67-77.
Goeders et al., Non-contingent electric footshock facilitates the acquisition of intravenous cocaine self-administration in rats. Psychopharmacology (Berl). Feb. 1994;114(1)163-70.
Goeders et al., Potential role for the hypothalamo-pituitary-adrenal axis in the conditioned reinforcer-induced reinstatement of extinguished cocaine seeking in rats. Psychopharmacology (Berl). May 2002;161(3):222-32.
Goeders et al., Role of corticosterone in intravenous cocaine self-administration in rats. Neuroendocrinology. Nov. 1996,64(5):337-48.
Goeders et al., The combination of metyrapone and oxazepam for the treatment of cocaine and other drug addictions. Adv Pharmacol. 2014;69:419-79.
Goeders et al., The combination of metyrapone and oxazepam reduces intravenous nicotine self-administration in rats. ACNP 49th Annual Meeting. Abstract 2010-PS-1178-ACNP, Aug. 23, 2010.
Goeders, A neuroendocrine role in cocaine reinforcement. Psychoneuroendocrinology. May 1997;22(4):237-59.
Goeders, Stress and cocaine addiction. J Pharmacol Exp Ther. Jun. 2002;301(3):785-9.
Goeders, Stress, Motivation, and Drug Addiction. Current Directions in Psychological Science. 2004;13(1):33-35.
Goeders, The HPA axis and cocaine reinforcement. Psychoneuroendocrinology. Jan.-Feb. 2002;27(1-2):13-33.
Goeders, The impact of stress on addiction. Eur Neuropsychopharmacol. Dec. 2003;13(6):435-41.
Goldstein et al., Drug addiction and its underlying neurobiological basis: neuroimaging evidence for the involvement of the frontal cortex. Am J Psychiatry. Oct. 2002;159(10):1642-52.
Guerin et al., Combination pharmacotherapy targeting the HPA axis and its effects on cocaine self-adminislialion in rats. Neuroscience. Nov. 15, 2001;Abstract No. 978.3, 2 pages.
Guerin et al., Effects of metyrapol on cocaine self-administration in rats. Neuroscience. Nov. 18, 2008;Abstract 661.4, 1 page.
Gurkovskaya et al., Effects of CP-154,526 on responding during extinction from cocaine self-administration in rats. Eur J Pharmacol. Nov. 30, 2001;432(1):53-6.
Haleem et al., Adaptation of female rats to stress: shift to male pattern by inhibition of corticosterone synthesis. Brain Res. Aug. 23, 1988;458(2):339-47.
Haynes, Adrenocorticotropic Hormone; Adrenocortical Steroids and Their Synthetic Analogs; Inhibitors of the Synthesis and Actions of Adrenocortical Hormones. Goodman and Gilman's The Pharmacological Basis of Therapeutics, Eighth Edition. Pergamon Press, New York. Chapter 60, pp. 1431-1462, (1990).
Heesch et al., Effects of cocaine on cortisol secretion in humans. Am J Med Sci. Aug. 1995;310(2):61-4.
Helene et al., Control of gene expression by triple helix-forming oligonucleotides. The antigene strategy. Ann N Y Acad Sci. Oct. 28, 1992;660:27-36.
Helene, The anti-gene strategy: control of gene expression by triplex-forming-oligonucleotides. Anticancer Drug Des. Dec. 1991;6(6):569-84.
Hyrup et al., Peptide nucleic acids (PNA): synthesis, properties and potential applications. Bioorg Med Chem. Jan. 1996;4(1):5-23.
Ichimura, Studies on the hypothalamo-pituitary adrenal axis in children by using 11-beta-hydroxylase inhibitors. Folia Endocrinol Jap. 1983;59(5):715-37.
Inoue et al., Sequence-dependent hydrolysis of RNA using modified oligonucleotide splints and RNase H. FEBS Lett. May 11, 1987;215(2):327-30.
Inoue et al., Synthesis and hybridization studies on two complementary nona(2'-O-methyl)ribonucleotides. Nucleic Acids Res. Aug. 11, 1987;15(15):6131-48.
Javaid et al., Peripheral benzodiazepine receptors are decreased during cocaine withdrawal in humans. Biol Psychiatry. Jul. 1, 1994;36(1):44-50.

(56) References Cited

OTHER PUBLICATIONS

Joels et al., Mineralocorticoid and glucocorticoid receptors in the brain. Implications for ion permeability and transmitter systems. Prog Neurobiol. May 1994;43(1):1-36.

Kablinger et al., Effects of the combination of metyrapone and oxazepam on cocaine craving and cocaine taking: a double-blind, randomized, placebo-controlled pilot study. J Psychopharmacol. Jul. 2012;26(7):973-81.

Keller et al., Combinations of oxazepam and metyrapone attenuate cocaine and methamphetamine cue reactivity. Drug Alcohol Depend. Dec. 1, 2013;133(2):405-12.

Kleber, Pharmacotherapy, Current and Potential, for the Treatment of Cocaine Dependence. Clinical Neuropharmacology. 1995;18(Suppl. 1):S96-S109.

Kreek et al., Pharmacotherapy of addictions. Nat Rev Drug Discov. Sep. 2002;1(9):710-26.

Krupitsky et al., Clinical trial of escitalopram for alcoholism comorbid with affective disorders. European Neuropsychopharmacology. 2010;20:S571, Abstract P.6.a.002.1 page.

Kuipers et al., Inhibition and induction of bile acid synthesis by ketoconazole. Effects on bile formation in the rat. Lipids. Sep. 1989;24(9):759-64.

Lamberts et al., Differential effects of the imidazole derivatives etomidate, ketoconazole and miconazole and of metyrapone on the secretion of cortisol and its precursors by human adrenocortical cells. J Pharmacol Exp Ther. Jan. 1987;240(1):259-64.

Lamon et al., Stress among males recovering from substance abuse. Addict Behav. Mar.-Apr. 1997;22(2):195-205.

Levin et al., Life-threatening serotonin toxicity due to a citalopram-fluconazole drug interaction: case reports and discussion. Gen Hosp Psychiatry. Jul.-Aug. 2008;30(4):372-7.

Licinio et al., The hypothalamic-pituitary-adrenal axis in anorexia nervosa. Psychiatry Res. Apr. 16, 1996;62(1):75-83.

Loose et al., Ketoconazole binds to glucocorticoid receptors and exhibits glucocorticoid antagonist activity in cultured cells. J Clin Invest. Jul. 1983;72(1):404-8.

Luchetti et al., Neurosteroid and GABA-A receptor alterations in Alzheimer's disease, Parkinson's disease and multiple sclerosis. Neuroscience. Sep. 15, 2011;191:6-21.

Mackenzie et al., Expression of 11beta-hydroxylase and aldosterone synthase genes in the rat brain. J Mol Endocrinol. Jun. 2000;24(3):321-8.

Maher et al., DNA triple-helix formation: an approach to artificial gene repressors? Bioessays. Dec. 1992;14(12):807-15.

Mantsch et al., Corticosterone facilitates the acquisition of cocaine self-administration in rats: opposite effects of the type II glucocorticoid receptor agonist dexamethasone. J Pharmacol Exp Ther. Oct. 1998;287(1):72-80.

Mantsch et al., Effects of cocaine self-administration on plasma corticosterone in rats: relationship to hippocampal type II glucocorticoid receptors. Prog Neuropsychopharmacol Biol Psychiatry. May 2000;24(4):633-46.

Mantsch et al., Ketoconazole blocks the stress-induced reinstatement of cocaine-seeking behavior in rats: relationship to the discriminative stimulus effects of cocaine. Psychopharmacology (Berl). Mar. 1999;142(4):399-407.

Mantsch et al., Ketoconazole does not block cocaine discrimination or the cocaine-induced reinstatement of cocaine-seeking behavior. Pharmacol Biochem Behav. Sep. 1999;64(1):65-73.

Mendelson et al., Buprenorphine attenuates the effects of cocaine on adrenocorticotropin (ACTH) secretion and mood states in man. Neuropsychopharmacology. Sep. 1992;7(2):157-62.

Mendelson et al., Effects of low- and high-nicotine cigarette smoking on mood states and the HPA axis in men. Neuropsychopharmacology. Sep. 2005;30(9):1751-63.

Mueller et al., Differential regulation of glucocorticoid synthesis in murine intestinal epithelial versus adrenocortical cell lines. Endocrinology. Mar. 2007;148(3):1445-53.

Murphy et al., Response to steroid suppression in major depression resistant to antidepressant therapy. J Clin Psychopharmacol. Apr. 1991;11(2):121-6.

Nagai et al., Effect of ketoconazole, etomidate and other inhibitors of steroidogenesis on cytochrome P-450sccll-catalyzed reactions. J Steroid Biochem. Sep. 1987;28(3):333-6.

Nagamine et al., Stereoselective reductive metabolism of metyrapone and inhibitory activity of metyrapone metabolites, metyrapol enantiomers, on steroid 11 beta-hydroxylase in the rat. Biol Pharm Bull. Feb. 1997;20(2):188-92.

Ohyama et al., Isolation and characterization of a cytochrome P-450 from rat kidney mitochondria that catalyzes the 24-hydroxylation of 25-hydroxyvitamin D3. J Biol Chem. May 15, 1991;266(14):8690-5.

Oliveira et al., Anti-Candida Activity of Fluoxetine Alone and Combined with Fluconazole: a Synergistic Action against Fluconazole-Resistant Strains. Antimicrob Agents Chemother. Jul. 2014;58(7):4224-6.

Parnham et al., The influence of metyrapone on the synthesis and release of prostaglandins from the pregnant rat uterus in vitro. Br J Pharmacol. Dec. 1975;55(4):535-9.

Patel et al., Endocannabinoid signaling negatively modulates stress-induced activation of the hypothalamic-pituitary-adrenal axis. Endocrinology. Dec. 2004;145(12):5431-8.

Peltier et al., Effects of saline substitution on responding and plasma corticosterone in rats trained to self-administer different doses of cocaine. J Pharmacol Exp Ther. Oct. 2001;299(1):114-20.

Perault-Staub et al., Thyroid function and plasma phosphate level in rat. Endocrinology. Feb. 1972;90(2):558-62.

Perry-O'Keefe et al., Peptide nucleic acid pre-gel hybridization: an alternative to southern hybridization. Proc Natl Acad Sci USA. Dec. 10, 1996;93(25):14670-5.

Piazza et al., Inhibition of corticosterone synthesis by Metyrapone decreases cocaine-induced locomotion and relapse of cocaine self-administration. Brain Res. Sep. 26, 1994;658(1-2):259-64.

Raven et al., The relationship between the effects of metyrapone treatment on depressed mood and urinary steroid profiles. Psychoneuroendocrinology. Apr. 1996;21(3):277-86.

Reuter et al., The role of cortisol suppression on craving for and satisfaction from nicotine in high and low impulsive subjects. Hum Psychopharmacol. Jul. 2002;17(5):213-24.

Rivier et al., Synthetic competitive antagonists of corticotropin-releasing factor: effect on ACTH secretion in the rat. Science. May 25, 1984;224(4651):889-91.

Rogoz et al., Effect of metyrapone on the fluoxetine-induced change in extracellular dopamine, serotonin and their metabolites in the rat frontal cortex. Pharmacol Rep. Nov.-Dec. 2010;62(6):1015-22.

Shaham et al., Stress-induced relapse to heroin and cocaine seeking in rats: a review. Brain Res Brain Res Rev. Aug. 2000;33(1):13-33.

Sinha, How does stress increase risk of drug abuse and relapse? Psychopharmacology (Berl). Dec. 2001;158(4):343-59.

Smagin et al., Effects of acute and chronic ketoconazole administration on hypothalamo-pituitary-adrenal axis activity and brain corticotropin-releasing hormone. Psychoneuroendocrinology. Nov. 2004,29(10):1223-8.

Sonino, Inhibition of Adrenal Steroid Biosynthesis by Metyrapone. Hormone Antagonists. M.K. Agarwal (Ed.), Walter de Gruyter & Co., Berlin. pp. 419-429, 1982.

PHARMACEUTICAL COMPOSITIONS AND USES THEREOF

RELATED APPLICATIONS

This application is a 35 U.S.C. § 371 national stage filing of International Application No. PCT/US2018/021939, filed on Mar. 12, 2018, which in turn claims the benefit of U.S. Provisional Application No. 62/469,798, filed on Mar. 10, 2017. The entire contents of each of the foregoing applications are incorporated herein by reference.

FIELD OF THE INVENTION

The present disclosure relates to pharmaceutical compositions and kits comprising metyrapone and oxazepam, and methods of treating diseases, such as addiction, using such compositions and kits.

BACKGROUND OF THE INVENTION

Therapeutics which include the combination of metyrapone and oxazepam are being developed to treat various substance use disorders (e.g., tobacco use disorder, cocaine use disorder). Accordingly, there is a need to provide shelf-stable pharmaceutical compositions comprising metyrapone and oxazepam that allow the combination therapy to be manufactured reproducibly and in high volume.

SUMMARY OF THE INVENTION

Under certain conditions, when oxazepam and metyrapone are combined directly, oxazepam may be degraded. The pharmaceutical compositions provided herein may be advantageous over existing compositions because of the limited contact or physical separation of the first (e.g., metyrapone) and second (e.g., oxazepam) active pharmaceutical components, thus reducing the amount of degradation of either of the active pharmaceutical components.

In one aspect, provided are pharmaceutical compositions comprising a first and a second active pharmaceutical component:

(i) wherein said first component comprises metyrapone or a pharmaceutically acceptable salt, co-crystal, solvate, hydrate, polymorph, isotopically enriched derivative, or prodrug thereof; and (ii) wherein said second component comprises oxazepam or a pharmaceutically acceptable salt, co-crystal, tautomer, stereoisomer, solvate, hydrate, polymorph, isotopically enriched derivative, or prodrug thereof;

wherein said metyrapone, and said oxazepam, are not in physical contact with each other.

In another aspect, provided are pharmaceutical compositions consisting essentially of a first and second active pharmaceutical component:

(i) wherein said first component comprises metyrapone or a pharmaceutically acceptable salt, co-crystal, solvate, hydrate, polymorph, isotopically enriched derivative, or prodrug thereof;
and (ii) wherein said second component comprises oxazepam or or a pharmaceutically acceptable salt, co-crystal, tautomer, stereoisomer, solvate, hydrate, polymorph, isotopically enriched derivative, or prodrug thereof;

wherein said metyrapone, and said oxazepam, are not in physical contact with each other.

In certain embodiments, the pharmaceutical compositions are in unit dosage form.

In another aspect, provided are methods of treating disorders associated with aberrant activity in the HPA axis (e.g., addiction to a substance) by administering the pharmaceutical compositions.

Also provided are uses and methods of preparing the pharmaceutical compositions, as well as kits providing the pharmaceutical compositions.

The details of certain embodiments of the invention are set forth herein. Other features, objects, and advantages of the invention will be apparent from the Detailed Description, Examples, and Claims.

Definitions

As used herein, the term "salt" refers to any and all salts and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response, and the like and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19. Pharmaceutically acceptable salts of the compounds of this invention include those derived from suitable inorganic and organic acids and bases. Examples of pharmaceutically acceptable, non-toxic acid addition salts are salts of an amino group formed with inorganic acids, such as hydrochloric acid, hydrobromic acid, phosphoric acid, and sulfuric acid, or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_1\text{-}C_4 \text{ alkyl})_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "polymer" is given its ordinary meaning as used in the art, i.e., a molecular structure comprising one or more repeat units (monomers), connected by covalent bonds. The repeat units may all be identical, or, in some cases, there may be more than one type of repeat unit present within the polymer. In certain embodiments, a polymer is a compound comprising eleven or more covalently connected repeating units. In certain embodiments, a polymer is naturally occurring. In certain embodiments, a polymer is synthetic (i.e., not naturally occurring).

The term "solvate" refers to forms of a compound, or a salt thereof, that are associated with a solvent, usually by a solvolysis reaction. This physical association may include hydrogen bonding. Conventional solvents include water, methanol, ethanol, acetic acid, dimethylsulfoxide (DMSO), tetrahydrofuran (THF), diethyl ether, and the like. The compounds described herein may be prepared, e.g., in crystalline form and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R.x\ H_2O$, wherein R is the compound and x is a number greater than 0. A given compound may form more than one type of hydrate, including, e.g., monohydrates (x is 1), lower hydrates (x is a number greater than 0 and smaller than 1, e.g., hemihydrates ($R.0.5\ H_2O$)), and polyhydrates (x is a number greater than 1, e.g., dihydrates ($R.2\ H_2O$) and hexahydrates ($R.6\ H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may be catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

The term "polymorph" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "co-crystal" refers to a crystalline structure composed of at least two components. In certain embodiments, a co-crystal contains a compound of the present invention and one or more other component, including, but not limited to, atoms, ions, molecules, or solvent molecules. In certain embodiments, a co-crystal contains a compound of the present invention and one or more solvent molecules. In certain embodiments, a co-crystal contains a compound of the present invention and one or more acid or base. In certain embodiments, a co-crystal contains a compound of the present invention and one or more components related to said compound, including, but not limited to, an isomer, tautomer, salt, solvate, hydrate, synthetic precursor, synthetic derivative, fragment, or impurity of said compound.

The term "prodrugs" refers to compounds that have cleavable groups and become by solvolysis or under physiological conditions the compounds described herein, which are pharmaceutically active in vivo. Such examples include, but are not limited to, choline ester derivatives and the like as well as N-alkylmorpholine esters and the like. Other derivatives of the compounds described herein have activity in both their acid and acid-derivative forms, but often offer advantages in the acid-sensitive form of solubility, tissue compatibility, or delayed release in the mammalian organism (see, Bundgard, H., Design of Prodrugs, pp. 7-9, 21-24, Elsevier, Amsterdam 1985). Prodrugs include, but are not limited to, acid derivatives well known to practitioners of the art, such as, for example, esters prepared by reaction of the parent alcohol with a suitable acid. Simple aliphatic or aromatic esters, amides, and anhydrides derived from alcohol or acidic groups pendant on the compounds described herein are particular prodrugs. In some cases, it is desirable to prepare double ester-type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, dogs, and/or birds (e.g., commercially relevant birds such as chickens, ducks, geese, and/or turkeys). In certain embodiments, the animal is a mammal. The animal may be a male or female and at any stage of development. A non-human animal may be a transgenic or genetically engineered animal.

The terms "administer," "administering," or "administration" refer to implanting, absorbing, ingesting, injecting, inhaling, or otherwise introducing a drug delivery composition as described herein.

The terms "treatment," "treat," and "treating" refer to reversing, alleviating, delaying the onset of, or inhibiting the progress of a "pathological condition" (e.g., a disease, disorder, or condition, including one or more signs or symptoms thereof) described herein. In some embodiments, treatment may be administered after one or more signs or symptoms have developed or have been observed. Treatment may also be continued after symptoms have resolved, for example, to delay or prevent recurrence and/or spread.

The terms "condition," "disease," and "disorder" are used interchangeably.

An "effective amount" is an amount sufficient to elicit a desired biological response, i.e., treating the condition. As will be appreciated by those of ordinary skill in this art, the effective amount of drug delivery composition may vary depending on such factors as the desired biological endpoint, the pharmacokinetics of the therapeutic agents in the composition, the condition being treated, and the age and health of the subject. An effective amount encompasses therapeutic and prophylactic treatment.

A "therapeutically effective amount" is an amount sufficient to provide a therapeutic benefit in the treatment of a condition or to delay or minimize one or more symptoms associated with the condition. A therapeutically effective amount of an inventive composition means an amount of therapeutic agent(s), alone or in combination with other therapies, that provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" is an amount sufficient to prevent a condition, or one or more symptoms associated with the condition or prevent its recurrence. A prophylactically effective amount of a composition means an amount of therapeutic agent(s), alone or in combination with other agents, that provides a prophylactic benefit in the prevention of the condition. The term "prophylactically effective amount" can encompass an amount that improves overall prophylaxis or enhances the prophylactic efficacy of another prophylactic agent.

The term "prevent," "preventing," or "prevention" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population.

The term "small molecule" or "small molecule therapeutic" refers to molecules, whether naturally occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and not more than about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460; drugs for veterinary use are listed by the FDA under 21 C.F.R. §§ 500 through 589. All listed drugs are considered acceptable for use in accordance with the present invention.

The term "pharmaceutical component" refers to any substance having pharmaceutical and/or therapeutic properties that produce a desired, usually beneficial, effect. For example, pharmaceutical components may treat, ameliorate, and/or prevent disease. Pharmaceutical components, as disclosed herein, may be small molecule therapeutics.

The term "therapeutic agent" refers to any substance having therapeutic properties that produce a desired, usually beneficial, effect. For example, therapeutic agents may treat, ameliorate, and/or prevent disease. Therapeutic agents, as disclosed herein, may be small molecule therapeutics.

DETAILED DESCRIPTION

Provided herein are pharmaceutical compositions. The pharmaceutical compositions comprise a first and a second active pharmaceutical component. The first component may comprise metyrapone, or a pharmaceutically acceptable salt thereof. The second component may comprise oxazepam, or a pharmaceutically acceptable salt thereof. The first and second active pharmaceutical components (e.g., metyrapone and oxazepam) may not be in physical contact with each other. The pharmaceutical compositions may further comprise one or more pharmaceutically acceptable excipients (e.g., fillers, inert diluents, dispersing agents, granulating agents, surface-active agents, emulsifiers, disintegrating agents, binding agents, preservatives, buffering agents, glidants, lubricating agents, solubilizing agents, and oils). The pharmaceutical compositions may be useful in the treatment of disorders associated with aberrant activity in the HPA axis, thus providing unique compositions for the treatment of disorders such as addiction.

Pharmaceutical Compositions

Metyrapone

The pharmaceutical compositions include metyrapone (1), or a pharmaceutically acceptable salt, co-crystal, solvate, hydrate, polymorph, isotopically enriched derivative, or prodrug thereof. Reference to metyrapone herein includes reference to any pharmaceutically acceptable salt, co-crystal, solvate, hydrate, polymorph, isotopically enriched derivative, or prodrug of metyrapone.

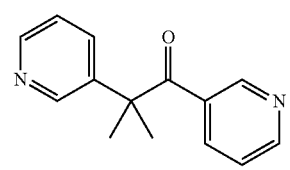

(1)

Metyrapone (METOPIRONE®) is a drug useful in the diagnosis of adrenal insufficiency and in the treatment of Cushing's syndrome (hypercortisolism). Metyrapone blocks cortisol synthesis by reversibly inhibiting steroid 11β-hydroxylase. This stimulates ACTH secretion, which in turn increases plasma 11-deoxycortisol levels. Accordingly, metyrapone affects physiological systems related to stress and the subsequent activation of the hypothalamic-pituitary-adrenal (HPA) axis.

The composition comprises, by weight, about 10% to about 95%, about 10% to about 90%, about 10% to about 80%, about 10% to about 70%, about 10% to about 60%, about 10% to about 50%, about 20% to about 50%, about 30% to about 50%, about 30% to about 45%, about 30% to about 40%, about 40% to about 50%, about 40% to about 45%, or about 35% to about 40% of the metyrapone. The composition comprises, by weight, about 10%, about 15%, about 20%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 65%, about 70%, about 75%, about 80%, about 85%, about 90%, or about 95% of the metyrapone.

Oxazepam

The pharmaceutical compositions include oxazepam (2), or a pharmaceutically acceptable salt, co-crystal, tautomer, stereoisomer, solvate, hydrate, polymorph, isotopically enriched derivative, or prodrug thereof. Reference to oxazepam herein includes reference to any pharmaceutically acceptable salt, co-crystal, tautomer, stereoisomer, solvate, hydrate, polymorph, isotopically enriched derivative, or prodrug of oxazepam.

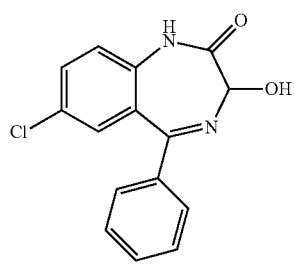

(2)

Oxazepam is an intermediate-acting benzodiazepine of the 3-hydroxy family; it acts on benzodiazepine receptors, resulting in increased effect of GABA to the $GABA_A$ receptor, which results in inhibitory effects on the central nervous system. Oxazepam is used for the treatment of anxiety and insomnia and in the control of symptoms of alcohol withdrawal, and has moderate amnesic, anxiolytic, anticonvulsant, hypnotic, sedative, and skeletal muscle relaxant properties compared to other benzodiazepines. Accordingly, oxazepam targets the prefrontal cortex by targeting GABA.

The composition comprises, by weight, about 1% to about 40%, about 1% to about 30%, about 1% to about 20%, about 1% to about 10%, about 1% to about 5%, about 1% to about 4%, about 1% to about 3%, or about 1% to about 2% of the oxazepam. The composition comprises, by weight, about 1%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.5%, about 4%, about 5%, about 10%, about 15%, about 20%, about 25%, about 30%, about 35%, or about 40% of the oxazepam.

In certain embodiments, the ratio, by weight, of metyrapone to oxazepam in the pharmaceutical composition is about 1:1 to about 100:1, about 1:1 to about 50:1, about 2:1 to about 50:1, about 5:1 to about 50:1, about 10:1 to about 50:1, about 10:1 to about 40:1, about 10:1 to about 30:1, about 20:1 to about 30:1, about 20:1 to about 25:1, or about 25:1 to about 30:1. In certain embodiments, the ratio, by weight, of metyrapone to oxazepam is about 1:1, about 2:1, about 5:1, about 10:1, about 15:1, about 16:1, about 17:1, about 18:1, about 19:1, about 20:1, about 21:1, about 22:1, about 22.5:1, about 23:1, about 24:1, about 25:1, about 26:1, about 27:1, about 28:1, about 29:1, about 30:1, about 35:1, about 40:1, about 50:1, about 60:1, about 70:1, about 80:1, about 90:1, or about 100:1.

Excipients

The pharmaceutical compositions may further comprise one or more pharmaceutically acceptable excipients. The pharmaceutically acceptable excipients may impart certain advantageous properties on the compositions (e.g., manufacturability, flowability, stability). The pharmaceutically acceptable excipients include fillers, dispersing and/or granulating agents, surface-active agents and/or emulsifiers, disintegrating agents, binding agents, preservatives, buffering agents, glidants, lubricating agents, solubilizing agents, coating agents, and/or oils. Excipients such as cocoa butter and suppository waxes, and coloring agents may also be present in the composition.

Exemplary fillers include mannitol, lactose, sucrose, dextrose, maltodextrin, sorbitol, xylitol, inositol, cellulose, powdered cellulose, microcrystalline cellulose, silicified microcrystalline cellulose, methylcellulose, ethylcellulose, hydroxyethylcellulose, methylhydroxyethylcellulose, powdered sugar, starch, pregelatinized starch, cornstarch, sodium phosphate lactose, kaolin, sodium chloride, calcium phosphate, dibasic calcium phosphate, calcium sulfate, calcium carbonate, sodium carbonate, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM®), sodium lauryl sulfate, quaternary ammonium compounds, and mixtures thereof.

Exemplary surface active agents and/or emulsifiers and/or wetting agents include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and VEEGUM® (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (TWEEN® 20), polyoxyethylene sorbitan (TWEEN® 60), polyoxyethylene sorbitan monooleate (TWEEN® 80), sorbitan monopalmitate (SPAN® 40), sorbitan monostearate (SPAN® 60), sorbitan tristearate (SPAN® 65), glyceryl monooleate, sorbitan monooleate (SPAN® 80)), polyoxyethylene esters (e.g., polyoxyethylene monostearate (MYRJ 45), polyoxyethylene hydrogenated castor oil, polyethoxylated castor oil, polyoxymethylene stearate, and Solutol), sucrose fatty acid esters, polyethylene glycol fatty acid esters (e.g., CREMOPHOR®, polyoxyethylene ethers, (e.g., polyoxyethylene lauryl ether (BRIJ® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, PLURONIC® F-68, Poloxamer-188, cetrimonium bromide, cetylpyridinium chloride, benzalkonium chloride, docusate sodium, and/or mixtures thereof.

Exemplary disintegrating agents include croscarmellose sodium, sodium alginate, calcium alginate, alginic acid, starch, pregelatinized starch, sodium starch glycolate, crospovidone, cellulose and its derivatives, carboxymethylcellulose calcium, carboxymethylcellulose sodium, soy polysaccharide, guar gum, an ion exchange resin, an effervescent system based on food acids and an alkaline carbonate component, and sodium bicarbonate.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (VEEGUM®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary preservatives include antifungal preservatives, alcohol preservatives, acidic preservatives, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT PLUS®, PHENONIP®, methylparaben, GERMALL® 115, GERMABEN® II, NEOLONE®, KATHON®, and EUXYL®.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary glidants include silicon dioxide, colloidal silicon dioxide, e.g. colloidal silica anhydrous, e.g., AEROSIL® 200, magnesium trisilicate, powdered cellulose, starch, talc, and polyethylene glycol.

Exemplary lubricating agents include magnesium stearate, calcium stearate, sodium stearate, glyceryl monostearate, sodium stearyl fumarate, stearic acid, silica, talc, fatty acid, fatty alcohol, fatty acid ester, malt, glyceryl behanate, hydrogenated oils, vegetable oil, mineral oil, polyethylene glycol, sodium benzoate, sodium acetate, sodium chloride, leucine, magnesium lauryl sulfate, sodium lauryl sulfate, leucine, and mixtures thereof.

Exemplary solubilizing agents include ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycol, glycerine, cyclodextrins, benzalkonium chloride, benzethonium chloride, cetylpyridinium chloride, docusate sodium, nonoxynol 9, octoxymol 9, poloxamer, poloxamer 124, poloxamer 188, poloxamer 237, poloxamer 338, poloxamer 407, polyoxyl 35 castor oil, polyoxyl 40 hydrogenaed castor oil, polyoxyl 10 oleyl ether, polyoxyl 20 cetostearyl ether, polyoxyl 40 stearate, polysorbate 20, polysorbate 40, polysorbate 60, polysorbate 80, sodium lauryl sulfate, sorbitan monolaurate, sorbitan monooleate, sorbitan monopalmitate, sorbitan monostearate, tyloxapo, and mixtures thereof.

Exemplary coating agents include polymers such as polyvinyl pyrrolidone, hydroxypropyl methylcellulose, hydroxypropyl cellulose, polyvinyl alcohol (PVA), propylene glycol, polyethylene glycol (PEG), methacrylic acid copolymers, cellulose acetate butyrate, cellulose acetate trimellitate, carboxymethylethylcellulose, shellac, copolymers of methacrylic acid and/or methacrylic acid methyl esters (e.g., EUDRAGIT®), hydroxypropyl methylcellulose acetate succinate, hydroxypropyl methylcellulose phthalate, polyvinyl acetate phthalate, cellulose acetate phthalate, poloxamers (e.g., LUTROL® F68, LUTROL® F127, LUTROL® F108), or mixtures thereof. The coating agent may also include triacetin, dibutyl sebecate, tributyl citrate, triethyl citrate, acetyltriethyl citrate, acetyltributyl citrate, dibutyl phthalate, diethyl phthalate, dimethyl phthalate, glycerine, propylene glycol, benzyl benzoate, 2-pyrrolidone, N-methylpyrrolidone, chlorobutanol, sorbitol, and/or diacetin. Commercially available coating agents comprising film-forming polymers include coating agents useful for immediate release coatings (e.g., OPADRY®, OPADRY® II, OPADRY® QX, OPADRY® amb II, OPADRY® fx™, OPALUX®); coating agents useful for enteric release coatings (e.g., ACRYL-EZE®, ACRYL-EZE® II, ENTERACT®, OPADRY® Enteric, NUTRATERIC®, SURETERIC®); coating agents useful for sustained release coatings (SURELEASE®, ETHOCEL®, ETHOCEL® HP, OPADRY® CA, OPADRY® EC).

Exemplary oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

The composition comprises, by weight, about 5% to about 90%, about 10% to about 80%, about 10% to about 70%, about 10% to about 60%, about 10% to about 50%, about 20% to about 60%, about 30% to about 70%, about 30% to about 80%, about 50% to about 80%, about 60% to about 80%, about 60% to about 90%, or about 65% to about 75% of one or more pharmaceutically acceptable excipients. The one or more pharmaceutically acceptable excipients may be any combination of those excipients listed above.

Formulation of the Pharmaceutical Composition, Kits, and Administration

The present disclosure provides pharmaceutical compositions comprising active pharmaceutical components (i.e., therapeutic agents), as described herein. In certain embodiments, the pharmaceutical components are provided in an effective amount in the compositions to treat and/or prevent a disease (e.g., addiction). In certain embodiments, the effective amount is a therapeutically effective amount of metyrapone. In certain embodiments, the effective amount is a therapeutically effective amount of oxazepam.

In certain embodiments, the pharmaceutical components are provided in an ineffective amount in the compositions to treat and/or prevent a disease (e.g., addiction). For example, the amount of metyrapone in the composition may be an amount that is ineffective in providing a therapeutic effect when administered alone. Likewise, the amount of oxazepam in the composition may be an amount that is ineffective in providing a therapeutic effect when administered alone. However, when the individually ineffective doses of metyrapone and oxazepam are administered in combination in the composition, a therapeutic effect is achieved. This results from a synergistic effect of the combination of metyrapone and oxazepam.

The compositions and described herein can be prepared by any method known in the art of pharmacology. The compositions provided herein are typically formulated in a size (e.g., volume) and weight appropriate for the intended use (e.g., oral dosage) for ease of administration. It will be understood, however, that the total amount of the composition of the present disclosure (e.g., number of dosage forms) will be decided by the attending physician within the scope of sound medical judgment. The specific therapeutically effective dose level for any particular subject or organism will depend upon a variety of factors including the disease being treated and the severity of the disorder; the activity of the specific active ingredients employed; the specific composition employed; the age, body weight, general health, sex, and diet of the subject; the time of administration, route of administration, and rate of excretion of the specific active ingredients employed; the duration of the treatment; the drugs used in combination or coincidental with the specific active ingredients employed; and like factors well known in the medical arts.

The exact amount of the therapeutic agents required to achieve effective amounts will vary from subject to subject, depending, for example, on species, age, and general condition of a subject, severity of the side effects or disorder, identity of the particular agent(s), and the like.

In certain embodiments, an effective amount of the composition for administration to a 70 kg adult human may comprise about 0.0001 mg to about 5000 mg, about 0.0001 mg to about 4000 mg, about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg of the composition. In certain embodiments, an effective amount of metyrapone for administration to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 5 to about 1500 mg, about 1 mg to about 1000 mg, about 1 mg to about 800 mg, about 200 mg to about 800 mg, about 250 mg to about 300 mg, about 500 mg to about 600 mg, about 600 mg to about 700 mg, about 1 mg to about 100 mg, about 10 mg to about 1000 mg, or about 100 mg to about 1000 mg of the metyrapone. In certain embodiments, an effective amount of oxazepam for administration to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 5 mg to about 60 mg, about 5 mg to about 30 mg, or about 10 mg to about 30 mg, of the oxazepam.

In certain embodiments, the composition may be at dosage levels sufficient to deliver about 0.001 mg/kg to about 100 mg/kg, about 0.01 mg/kg to about 50 mg/kg, about 0.1 mg/kg to about 40 mg/kg, about 0.5 mg/kg to about 30 mg/kg, about 0.01 mg/kg to about 10 mg/kg, about 0.1 mg/kg to about 10 mg/kg, or about 1 mg/kg to about 25 mg/kg, of subject body weight per day, of any of the active pharmaceutical components present in the composition, to obtain the desired therapeutic effect.

Although the descriptions of the pharmaceutical compositions provided herein are principally directed to compositions which are suitable for administration to humans, it will be understood by the skilled artisan that such compositions are generally suitable for administration to animals of all sorts. Modification of drug delivery compositions suitable for administration to humans in order to render the compositions suitable for administration to various animals is well understood, and the ordinarily skilled veterinary pharmacologist can design and/or perform such modification with ordinary experimentation.

The compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the pharmaceutical composition described herein is suitable for topical administration to the eye of a subject.

Dosage Forms

The pharmaceutical compositions can be prepared, packaged, and/or sold in bulk, as a unit dosage form, and/or as a plurality of unit dosage forms. A "unit dosage form" is a discrete amount of the composition comprising a predetermined amount of the pharmaceutical components. The amount of the pharmaceutical components is generally equal to the dosage of the pharmaceutical components which would be administered to a subject and/or a convenient fraction of such a dosage, such as, for example, one-half, one-third, or one-quarter of such a dosage. The pharmaceutical compositions may be in unit dosage form.

In certain embodiments, the unit dosage form comprises a first active pharmaceutical component (e.g., metyrapone) and a second active pharmaceutical component (e.g., oxazepam) such that there is limited physical contact between the first and second active pharmaceutical components. In certain embodiments, there is essentially no physical contact between the first and second active pharmaceutical components. In certain embodiments, there is no physical contact between the first and second active pharmaceutical components. In certain embodiments, the first and second active pharmaceutical components are not in physical contact with each other. In certain embodiments, metyrapone and oxazepam are not in physical contact with each other. In certain embodiments, metyrapone and oxazepam are essentially not in physical contact with each other.

In certain embodiments, the pharmaceutical composition comprises a plurality of unit dosage forms which comprise metyrapone and oxazepam in separate unit dosage forms. When the pharmaceutical composition comprises a plurality of unit dosage forms wherein metyrapone and oxazepam are in separate unit dosage forms, the metyrapone and oxazepam unit dosage forms may be administered sequentially or administered concurrently.

In certain embodiments, the unit dosage form comprises solid dosage forms for oral administration. These solid dosage forms include capsules, tablets, dragees, pills, powders, beads, and granules. In such solid dosage forms, the active ingredient is mixed with at least one inert, pharmaceutically acceptable excipient or carrier such as fillers, binding agents, humectants such as glycerol, disintegrating agents, solution retarding agents such as paraffin, absorption accelerators such as quaternary ammonium compounds, wetting agents such as, for example, cetyl alcohol and glycerol monostearate, absorbents such as kaolin and bentonite clay, and lubricating agents. In the case of capsules, tablets, and pills, the dosage form may include a buffering agent. The solid dosage forms may also include a coating agent.

The active pharmaceutical component(s) can be in a micro-encapsulated form with one or more excipients as noted above. The solid dosage forms of tablets, dragees, capsules, pills, beads, and granules can be prepared with coatings and shells such as enteric coatings, release controlling coatings, and other coatings well known in the pharmaceutical formulating art. They may optionally comprise opacifying agents and can be of a composition that they release the active ingredients only, or preferentially, in a certain part of the intestinal tract, optionally, in a delayed manner. Examples of encapsulating compositions which can be used include polymeric substances and waxes. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents.

In certain embodiments, the unit dosage form is an oral dosage form selected from the group consisting of a tablet; a mini-tab; a capsule; a dragee; a lozenge; an orally disintegrating tablet; a dissolvable sheet; and a caplet.

In certain embodiments, the composition comprises a capsule. The capsule comprises metyrapone and oxazepam. In certain embodiments, the metyrapone component has an inert coating such that it is physically separate from the oxazepam component. In certain embodiments, the oxazepam component has an inert coating such that it is physically separate from the metyrapone component. The metyrapone component may comprise particles, granules, beads, pellets, minitabs, or a combination thereof. The oxazepam component may comprise particles, granules, beads, pellets, minitabs, or a combination thereof. Therefore, the capsule comprises distinct individual forms (e.g., particles, granules, beads, pellets, minitabs) of metyrapone and oxazepam, which may not be in contact with each other. In certain embodiments, the capsule further comprises an inert coating.

In certain embodiments, particles are included as blends of metyrapone. The blends may comprise any of the particles as described herein. In certain embodiments, particles are included as blends of oxazepam. In certain embodiments, the particles are asymmetric. In certain embodiments, the particles are symmetric. The blends may comprise any of the particles as described herein. The particles may have a diameter of less than or equal to 10 mm, less than or equal to 5 mm, less than or equal to 3 mm, less than or equal to 1 mm, less than or equal to 500 μm, less than or equal to 400

µm, less than or equal to 300 µm, less than or equal to 200 µm, less than or equal to 100 µm, or less than or equal to 50 µm.

In certain embodiments, the granules are asymmetric. In certain embodiments, the granules are symmetric. The granules may have a diameter of less than or equal to 10 mm, less than or equal to 5 mm, less than or equal to 3 mm, less than or equal to 1 mm, less than or equal to 500 µm, less than or equal to 400 µm, less than or equal to 300 µm, less than or equal to 200 µm, less than or equal to 100 µm, or less than or equal to 50 µm.

In certain embodiments, the beads are asymmetric. In certain embodiments, the beads are symmetric. The beads may have a diameter of less than or equal to 10 mm, less than or equal to 5 mm, less than or equal to 3 mm, less than or equal to 1 mm, less than or equal to 500 µm, less than or equal to 400 µm, less than or equal to 300 µm, less than or equal to 200 µm, less than or equal to 100 µm, or less than or equal to 50 µm.

In certain embodiments, the pellets are asymmetric. In certain embodiments, the pellets are symmetric. The pellets may have a diameter of less than or equal to 10 mm, less than or equal to 5 mm, less than or equal to 3 mm, less than or equal to 1 mm, less than or equal to 500 µm, less than or equal to 400 µm, less than or equal to 300 µm, less than or equal to 200 µm, less than or equal to 100 µm, or less than or equal to 50 µm.

In certain embodiments, the minitabs are asymmetric. In certain embodiments, the minitabs are symmetric. The minitabs may have a diameter of less than or equal to 10 mm, less than or equal to 5 mm, less than or equal to 3 mm, less than or equal to 1 mm, less than or equal to 500 µm, less than or equal to 400 µm, less than or equal to 300 µm, less than or equal to 200 µm, less than or equal to 100 µm, or less than or equal to 50 µm.

In certain embodiments, the composition comprises a softgel form with a core and a gelatin coating. In certain embodiments, the core comprises a solution of metyrapone. In certain embodiments, the core comprises solid metyrapone. In certain embodiments, the core comprises a solution of oxazepam. In certain embodiments, the core comprises solid oxazepam. In certain embodiments, the core of the softgel form comprises only one active pharmaceutical component (e.g., metyrapone or oxazepam).

In certain embodiments, when the core of the softgel form comprises metyrapone, the unit dosage form further comprises a layer of oxazepam on the gelatin coating. In certain embodiments, the softgel form further comprises an inert coating on top of the oxazepam layer on the gelating coating. In certain embodiments, the softgel form further comprises an additional inert coating.

In certain embodiments, when the core of the softgel form comprises oxazepam, the unit dosage form further comprises a layer of metyrapone on the gelatin coating. In certain embodiments, the softgel form further comprises an inert coating on top of the metyrapone layer on the gelating coating. In certain embodiments, the softgel form further comprises an additional inert coating.

In certain embodiments, the composition comprises a tablet. In certain embodiments, the tablet is a bilayered tablet. In certain embodiments, the tablet is a trilayered tablet. In certain embodiments, the tablet is a multilayered tablet comprising 2, 3, 4, 5, 6, or 7 layers. In certain embodiments, the tablet comprises a layer of metyrapone and a layer of oxazepam. In certain embodiments, the tablet comprises an inert layer. In certain embodiments, the inert layer comprises a physical barrier between the metyrapone layer and the oxazepam layer. In certain embodiments, the tablet further comprises an inert coating.

In certain embodiments, the tablet comprises a core and an outer layer. In certain embodiments, the tablet further comprises an inert layer between the core and the outer layer. In certain embodiments, the core comprises metyrapone and the outer layer comprises oxazepam. In certain embodiments, the core comprises oxazepam and the outer layer comprises metyrapone. In certain embodiments, the tablet further comprises an inert coating.

In certain embodiments, the unit dosage form comprises liquid dosage forms for oral or parenteral administration. These dosage forms include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the compounds described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

In certain embodiments, the unit dosage form comprises compositions for rectal or vaginal administration. These dosage forms are typically suppositories which can be prepared by mixing the compounds described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredients.

In certain embodiments, the unit dosage form comprises compositions for topical and/or transdermal administration of a compound described herein. These dosage forms may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of active ingredients to the body. Such dosage forms can be prepared, for example, by dissolving and/or dispensing the active ingredients in the proper medium. Alternatively or additionally, the rate can be controlled by either providing a rate controlling membrane and/or by dispersing the active ingredients in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredients, although the concentration of the active ingredients can be as high as the solubility limit of the active ingredients in the solvent. Formulations for topical administration may further comprise one or more of the additional ingredients described herein.

In certain embodiments, the unit dosage form comprises a pharmaceutical composition in a formulation suitable for pulmonary administration via the buccal cavity. Such a formulation may comprise dry particles which comprise the active ingredients and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredients dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredients may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredients).

Pharmaceutical compositions described herein formulated for pulmonary delivery may provide the active ingredients in the form of droplets of a solution and/or suspension. Such formulations can be prepared, packaged, and/or sold as aqueous and/or dilute alcoholic solutions and/or suspensions, optionally sterile, comprising the active ingredients, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredients and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredients, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredients, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredients. Such powdered, aerosolized, and/or aerosolized formulations, when dispersed, may have an average particle and/or droplet size in the range from about 0.1 to about 200 nanometers, and may further comprise one or more of the additional ingredients described herein.

In certain embodiments, the unit dosage form comprises a pharmaceutical composition for ophthalmic administration. Such formulations may, for example, be in the form of eye drops including, for example, a 0.1-1.0% (w/w) solution and/or suspension of the active ingredients in an aqueous or oily liquid carrier or excipient. Such drops may further comprise buffering agents, salts, and/or one or more other of the additional ingredients described herein. Other opthalmically-administrable formulations which are useful include those which comprise the active ingredients in microcrystalline form and/or in a liposomal preparation. Ear drops and/or eye drops are also contemplated as being within the scope of this disclosure.

The exact amount of a composition required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell.

A composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity in treating a disease in a subject in need thereof, in preventing a disease in a subject in need thereof, in reducing the risk to develop a disease in a subject in need thereof,), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The additional pharmaceutical agents include, but are not limited to, neurological agents, anti-proliferative agents, anti-cancer agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, and pain-relieving agents. In certain embodiments, the additional pharmaceutical agent is a neurological agent (e.g., antidepressant, anxiolytic).

In another aspect, the present disclosure contemplates a pharmaceutical composition comprising a multiparticulate dosage form (i.e., sprinkle dosage form) which comprises sufficiently small particles, beads, or granules of the active ingredient(s) described herein to overcome swallowing issues with larger oral dosage forms. These "sprinkle formulations" employ small multiparticulates (e.g., particles, beads, granules) in a larger dosage form (e.g., capsule) that can either be swallowed or opened to disperse the multiparticulates or "sprinkles" in liquid or soft food for administration. Sprinkles have applications for special patient populations, such as infants and young children, as well as older adults.

In certain embodiments, the pharmaceutical composition comprises beads of oxazepam. In certain embodiments, the beads have an inert coating. In certain embodiments, the beads are asymmetric. In certain embodiments, the beads are symmetric. The beads may have a diameter of less than or equal to 10 mm, less than or equal to 5 mm, less than or equal to 3 mm, less than or equal to 1 mm, less than or equal to 500 µm, less than or equal to 400 µm, less than or equal to 300 µm, less than or equal to 200 µm, less than or equal to 100 µm, or less than or equal to 50 µm. In certain embodiments, the beads comprise less than or equal to 20 mg, 15 mg, 10 mg, 5 mg, 4 mg, 3 mg, 2 mg, or 1 mg of oxazepam.

In another aspect, the present disclosure contemplates a pharmaceutical composition comprising a high dosage form of metyrapone, allowing for fewer dosage forms when metyrapone is dosed as a single agent, or in combination. In certain embodiments, granules, particles, and/or blends of metyrapone may be formulated in a larger dosage form (e.g., a capsule) for the administration of larger dosages of metyrapone. In certain embodiments, the larger dosage form of metyrapone comprises greater than or equal to 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, 450 mg, or 500 mg of metyrapone.

Kits

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for treating a disease (e.g., addiction) in a subject in need thereof. In certain embodiments, the kits are useful for preventing a disease (e.g., addiction) in a subject in need thereof. In certain embodiments, the kits are useful for reducing the risk of developing a disease (e.g., addiction) in a subject in need thereof.

In certain embodiments, a kit described herein further includes instructions for using the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease (e.g., addiction) in a subject in need thereof. In certain embodiments, the kits and instructions provide for preventing a disease (e.g., addiction) in a subject in need thereof. In certain embodiments, the kits and instructions provide for reducing the risk of developing a disease (e.g., addiction) in a subject in need thereof. A kit described herein may include one or more additional pharmaceutical agents described herein as a separate composition.

In certain embodiments, the kit comprises a blister pack, wherein the blister pack comprises a unit dose of metyrapone, and a unit dose of oxazepam. In certain embodiments, the unit dose of metyrapone is in a separate blister from the unit dose of oxazepam. In certain embodiments the blister pack comprises sufficient metyrapone and oxazepam to treat a patient for 30 days. In yet other embodiments, the blister pack comprises sufficient doses of metyrapone and oxazepam to treat a patient for 60 days. In other embodiments, the blister pack comprises sufficient doses of metyrapone and oxazepam to treat a patient for 90 days. In certain embodiments, unit doses of metyrapone and unit doses of oxazepam are in the same blister.

Properties of the Pharmaceutical Compositions

The pharmaceutical compositions described herein may possess certain advantageous properties. These properties may include stability, release properties, and/or abuse deterrent properties.

In certain embodiments, less than or equal to 50%, less than or equal to 40%, less than or equal to 30%, less than or equal to 20%, less than or equal to 10%, less than or equal to 5%, less than or equal to 4%, less than or equal to 3%, less than or equal to 2%, less than or equal to 1%, less than or equal to 0.5%, or less than or equal to 0.1%, by weight, of the metyrapone degrades after storage for 2 weeks, 4 weeks, 6 weeks, 8 weeks, 3 months, 6 months, or 1 year at ambient temperature.

In certain embodiments, less than or equal to 50%, less than or equal to 40%, less than or equal to 30%, less than or equal to 20%, less than or equal to 10%, less than or equal to 5%, less than or equal to 4%, less than or equal to 3%, less than or equal to 2%, less than or equal to 1%, less than or equal to 0.5%, or less than or equal to 0.1%, by weight, of the metyrapone degrades after storage for 2 weeks, 4 weeks, 6 weeks, 8 weeks, 3 months, 6 months, or 1 year at ambient temperature at a relative humidity of about 60%.

In certain embodiments, less than or equal to 50%, less than or equal to 40%, less than or equal to 30%, less than or equal to 20%, less than or equal to 10%, less than or equal to 5%, less than or equal to 4%, less than or equal to 3%, less than or equal to 2%, less than or equal to 1%, less than or equal to 0.5%, or less than or equal to 0.1%, by weight, of the metyrapone degrades after storage for 2 weeks, 4 weeks, 6 weeks, 8 weeks, 3 months, 6 months, or 1 year at a temperature of about 40° C.

In certain embodiments, less than or equal to 50%, less than or equal to 40%, less than or equal to 30%, less than or equal to 20%, less than or equal to 10%, less than or equal to 5%, less than or equal to 4%, less than or equal to 3%, less than or equal to 2%, less than or equal to 1%, less than or equal to 0.5%, or less than or equal to 0.1%, by weight, of the metyrapone degrades after storage for 2 weeks, 4 weeks, 6 weeks, 8 weeks, 3 months, 6 months, or 1 year at a temperature of about 40° C. at a relative humidity of about 75%.

In certain embodiments, less than or equal to 50%, less than or equal to 40%, less than or equal to 30%, less than or equal to 20%, less than or equal to 10%, less than or equal to 5%, less than or equal to 4%, less than or equal to 3%, less than or equal to 2%, less than or equal to 1%, less than or equal to 0.5%, or less than or equal to 0.1%, by weight, of the oxazepam degrades after storage for 2 weeks, 4 weeks, 6 weeks, 8 weeks, 3 months, 6 months, or 1 year at ambient temperature.

In certain embodiments, less than or equal to 50%, less than or equal to 40%, less than or equal to 30%, less than or equal to 20%, less than or equal to 10%, less than or equal to 5%, less than or equal to 4%, less than or equal to 3%, less than or equal to 2%, less than or equal to 1%, less than or equal to 0.5%, or less than or equal to 0.1%, by weight, of the oxazepam degrades after storage for 2 weeks, 4 weeks, 6 weeks, 8 weeks, 3 months, 6 months, or 1 year at ambient temperature at a relative humidity of about 60%.

In certain embodiments, less than or equal to 50%, less than or equal to 40%, less than or equal to 30%, less than or equal to 20%, less than or equal to 10%, less than or equal to 5%, less than or equal to 4%, less than or equal to 3%, less than or equal to 2%, less than or equal to 1%, less than or equal to 0.5%, or less than or equal to 0.1%, by weight, of the oxazepam degrades after storage for 2 weeks, 4 weeks, 6 weeks, 8 weeks, 3 months, 6 months, or 1 year at a temperature of about 40° C.

In certain embodiments, less than or equal to 50%, less than or equal to 40%, less than or equal to 30%, less than or equal to 20%, less than or equal to 10%, less than or equal to 5%, less than or equal to 4%, less than or equal to 3%, less than or equal to 2%, less than or equal to 1%, less than or equal to 0.5%, or less than or equal to 0.1%, by weight, of the oxazepam degrades after storage for 2 weeks, 4 weeks, 6 weeks, 8 weeks, 3 months, 6 months, or 1 year at a temperature of about 40° C. at a relative humidity of about 75%.

The pharmaceutical compositions release the active therapeutic agents (i.e., active pharmaceutical components) under physiological conditions, such as within the body. Release of the therapeutic agents may occur at varying rates, depending on the other components of the composition and the formulation of the composition. For example, the release rate of the therapeutic agents (the time at which the therapeutic agents are no longer a part of the composition) may be on the order of minutes, hours, or days. The therapeutic agents may be released by various mechanisms, e.g., by dissolution, by diffusion, chemical activity, enzymatic activity, or cellular machinery. The compositions are sufficiently stable in vivo such that they deliver drug to the intended target in a suitable amount of time.

In certain embodiments, less than or equal to 90%, less than or equal to 80%, less than or equal to 70%, less than or equal to 60%, less than or equal to 50%, less than or equal to 40%, less than or equal to 30%, less than or equal to 20%, less than or equal to 10%, less than or equal to 5%, or less than or equal to 1% of the metyrapone is released in vivo within 7 days, 6 days, 5 days, 4 days, 3 days, 2 days, 1 day, 18 hours, 12 hours, 8 hours, 6 hours, 4 hours, 3 hours, 2 hours, 1 hours, 45 minutes, 30 minutes, 20 minutes, 15 minutes, or 10 minutes after administration of the composition.

In certain embodiments, less than or equal to 90%, less than or equal to 80%, less than or equal to 70%, less than or equal to 60%, less than or equal to 50%, less than or equal to 40%, less than or equal to 30%, less than or equal to 20%, less than or equal to 10%, less than or equal to 5%, or less than or equal to 1% of the oxazepam is released in vivo within 7 days, 6 days, 5 days, 4 days, 3 days, 2 days, 1 day, 18 hours, 12 hours, 8 hours, 6 hours, 4 hours, 3 hours, 2 hours, 1 hours, 45 minutes, 30 minutes, 20 minutes, 15 minutes, or 10 minutes after administration of the composition.

Recently, increased attention has been drawn to the recreational use and abuse of prescription pharmaceutical compositions. The abuse, or non-medicinal use, of prescription pharmaceutical compositions is an increasing problem. Accordingly, preventing the abuse of prescription pharmaceuticals through the development of abuse deterrent pharmaceutical compositions has become a high public health priority for the U.S. Food and Drug Administration (FDA). Prescription pharmaceutical compositions that are typically misused or abused include Central Nervous System (CNS) depressants prescribed for anxiety or sleep problems, such as oxazepam.

Manufacturing approaches that may be employed to produce abuse-deterrent formulations of the compositions include, but are not limited to, incorporation of an excipient that gels when mixed with water, alcohol, or other common solvents; incorporation of a physical barrier that resists crushing, dissolving, melting, or chemical extraction (e.g., hard plastic polymer coatings); formulation of crush-resistant tablets; chemically engineering prodrugs that require in vivo enzymatic cleavage to produce a pharmacological effect (e.g., an amidic linkage formed between the drug molecule and a single amino acid like lysine or a small (up to 15 amino acids) oligopeptide, an ester linkage formed between a hydroxyl group on the drug and a carboxylic group on the carrier, complexation with an ion exchange resin, complexation with a metal cation, complexation with a fatty acid); incorporation of an aversive ingredient (e.g., a flushing agent [niacin], emetic [ipecac], diuretic, or irritant [capsaicin]) intended to create an unpleasant experience and thereby deter further experimentation; and co-formulation with a sequestered antagonist or aversive agent that is released upon product tampering.

In certain embodiments, metyrapone and/or oxazepam may be modified in a manner as described above to produce abuse-deterrent compositions. In certain embodiments, the pharmaceutical compositions may be modified or formulated in a manner as described above to produce abuse-deterrent compositions.

Methods of Treatment and Uses

The compositions described herein can be used to treat patients suffering from a disorder associated with aberrant activity in the HPA axis. The treatment methods can include various steps, one of which can constitute identifying a patient in need of treatment. Physicians are well able to examine and diagnose patients suspected of suffering from addiction and/or another of the conditions described herein. Following a diagnosis, which may be made in the alternative, the physician can prescribe a therapeutically effective amount of a composition (e.g., a pharmaceutical composition comprising a first agent that targets the HPA axis and a second agent that targets the prefrontal cortex). The patient may have, or be diagnosed as having, an addiction to a substance such as alcohol, a chemical stimulant, a prescription (or prescribed) pain reliever, or a naturally-occurring plant-derived drug. The chemical stimulant can be cocaine, an amphetamine, methamphetamine, or crystalline methyl-amphetamine hydrochloride, or methylphenidate. Where analogs of specific drugs are addictive, addictions to those analogs can also be treated.

The drug may be a barbiturate (e.g., thiamyl (SURITAL®), thiopental (PENTOTHAL®), amobarbital (AMYTA®), pentobarbital (NEMBUTAL®), secobarbital (SECONAL®), Tuinal (an amobarbital/secobarbital combination product), butalbital (FIORINA®), butabarbital (BUTISOL®), talbutal (LOTUSATE®), aprobarbital (ALURATE®), phenobarbital (LUMINAL®), and mephobarbital (MEBARAL®)), or opiate (e.g., heroin, codeine, hydrocodone).

Naturally-occurring plant-derived drugs include marijuana and tobacco. The compositions described herein can be used to treat patients addicted to these substances generally and/or to a more specific ingredient therein (e.g., the nicotine in tobacco). The addiction may also manifest as addiction to an activity such as gambling, sex or a sexual activity, or overeating (which may be associated with an eating disorder or may result in obesity). More generally, eating and sleeping disorders are among those amenable to treatment with the present compositions. Eating disorders include anorexia nervosa, bulimia nervosa, binge eating disorder and eating disorders not otherwise specified (ED-NOS). Several studies have examined the function of the HPA axis in anorexia nervosa. A principal finding is that of hypercortisolism, associated with increased central corticotrophin-releasing hormone levels and normal circulating levels of adrenocorticotropic hormone. While anorexia nervosa can be difficult to diagnose, patients with this disorder present with endocrine dysfunction, often evident as amenorrhea, abnormal temperature regulation, abnormal growth hormone levels, and abnormal eating. The present methods can include a step of identifying a patient in need of treatment, and these characteristics would be, or would likely be among, those used by physicians to diagnose anorexia nervosa.

The compositions can be used to treat patients who have Prader Willi syndrome, and methods of treating such patients are within the scope of the disclosure.

Sleep disorders include insomnia, sleep apnea sleep disorder, Restless Legs Syndrome (RLS) and Periodic Limb Movement Disorder (PLMD), and narcolepsy.

Other patients amenable to treatment include those suffering from anxiety (which may be associated with panic disorder, obsessive compulsive disorder (OCD), post-traumatic stress disorder (PTSD), social anxiety disorder, or may be a generalized anxiety disorder). Where the condition is depression, it may be depression associated with major depressive disorder or dysthymia, bipolar depression, or may be associated with a medical condition or substance abuse. The risk of developing depression or other major affective disorders is determined by a complex interplay between genetic susceptibility, environmental exposures, and aging.

Other patients amenable to treatment include those suffering from schizophrenia; those with an attention-deficit disorder (e.g., ADD or ADHD); those experiencing menopause; and those suffering from a menstrual cycle-related syndrome (e.g., PMS).

The disorders and events described herein may be variously categorized and may be related to one another in various ways. For example, social anxiety may contribute to an eating disorder and other anxiety-associated conditions, such as PTDSs, may manifest as a sleep disorder. Patients diagnosed as clinically depressed may also experience sleep disorders. Addiction, which has been characterized as a progressive disorder, may begin with the self-administration of a prescription or non-prescription drug to alleviate a symptom of another neuropsychiatric disorder. For example, a patient may self-administer alcohol or marijuana in the event of a depression or anxiety or a sleep-aid to treat the difficulty in sleeping as a result thereof. The relationships between the disorders and related conditions or symptoms may flow in different directions as well. For example, chronic activation of the HPA axis in insomnia puts insomniacs at risk not only for mental disorders (i.e., chronic anxiety and depression), but also for significant medical morbidity associated with such activation. Insomnia is, by far, the most commonly encountered sleep disorder in medical practice. Either as a symptom of various psychiatric or medical disorders or as the result of a stressful situation, chronic and severe insomnia is perceived by the patient as a distinct disorder (see Vgontzas et al., *J. Clin. Endocrinol. Metabl.* 86:3787-3794, 2006). Sleep disorders, including insomnia, can occur during menopause or when a patient is suffering from PMS.

The success of the treatment can be assessed in a variety of ways, including objective measures (e.g., where the patient is addicted to a substance or activity, a reduction in the frequency or severity of drug self-administration or other addictive activity), a general improvement in health (e.g., an improvement in blood pressure, kidney function, liver function, or blood count) and/or subjective measures (e.g., a patient's report of reduced craving for a substance or activity or a better sense of well-being (e.g., where the patient suffers from anxiety or an anxiety-related disorder, a report of reduced anxiety, an improved mood, a greater sense of well-being, or an improved ability to cope with daily stressors)). Where the condition treated is an eating disorder or sleep disorder, treatment can be assessed by judging the effective return of (or return toward) normal eating or sleeping patterns.

In specific embodiments, the invention features methods of treating a patient who is suffering from a disorder associated with aberrant activity in the HPA axis. The method can include the steps of: (a) identifying a patient in need of treatment; and (b) administering to the patient a therapeutically effective amount of a composition described herein. The disorder can include addiction, anxiety, schizophrenia, or depression; the disorder can be an addiction to a substance (e.g., a chemical stimulant such as an opiate (e.g., heroin, codeine, hydrocodone, or analogs thereof), nicotine, alcohol, prescription pain reliever, or naturally-occurring plant-derived drug, such as nicotine). The chemical stimulant can also be cocaine, an amphetamine, a methamphetamine, methylphenidate, or analogs thereof.

The disorder can also be an addiction to an activity such as gambling or engaging in a sexual activity or excessive eating.

Where the patient is suffering from anxiety, the anxiety may be associated with a panic disorder, an obsessive compulsive disorder (OCD), a post-traumatic stress disorder (PTSD), a social anxiety disorder, or a generalized anxiety disorder. Where the patient is suffering from depression, the depression can be associated with major depressive disorder or dysthymia, with a bipolar depression, or a medical condition or substance abuse. As noted, the disorder can also be an eating disorder or a sleep disorder or a disruptive behavior disorder.

The methods can be carried out in treating a patient who is suffering from an unwanted symptom of menopause or the menstrual cycle by: (a) identifying a patient in need of treatment; and (b) administering to the patient a therapeutically effective amount of a composition described herein. The amounts of the compositions delivered are therapeutically effective, with effectiveness judged by relief in symptoms, which may include anxiety, depression, or difficulty sleeping.

The present disclosure provides methods of using the pharmaceutical compositions for the treatment and/or prevention of addiction to a substance in a subject. In certain embodiments, the substance is a chemical stimulant, opiate, nicotine, alcohol, prescription pain reliever, naturally occurring plant-derived drug or non-naturally occurring synthetic drug.

The present disclosure also includes the use of the compositions described herein in the preparation of a medicament. The present disclosure further features the use of the compositions described herein in the preparation of a medicament for the treatment of addiction to a substance; obesity; an eating disorder; a sleep disorder; depression; a disruptive behavior disorder; schizophrenia; and/or anxiety.

EXAMPLES

In order that the invention described herein may be more fully understood, the following examples are set forth. It should be understood that these examples are for illustrative purposes only and are not to be construed as limiting this invention in any manner.

Formulations

The formulations in Table 1 are made by processes known in the art or as described below.

TABLE 1

| | |
|---|---|
| 1 | Minitabs of metyrapone combined with minitabs of oxazepam in capsules. |
| 2 | Minitabs of metyrapone combined with minitabs of oxazepam in capsules; and one or both types of minitabs have an inert outer coating. |
| 3 | Beads of metyrapone combined with beads of oxazepam in capsules; and one or both types of beads of an outer coating. |
| 4 | Granules of metyrapone combined with beads of oxazepam in capsules; the beads of oxazepam have an outer coating; and, optionally, the granules of metyrapone are coated. |
| 5 | Granules of metyrapone combined with granules of oxazepam in capsules; the granules of oxazepam have an outer coating; and, optionally, the granules of metyrapone are coated. |
| 6 | Softgels having a solution of metyrapone, and the gelatin capsule is coated with oxazepam; optionally, an inert coating is present between the gelatin and the oxazepam; optionally, an inert coating is on top of the oxazepam layer. |
| 7 | Multilayer tablets in which one layer is a core of either metyrapone or oxazepam, with the core coated with an inert coating, and a coating of the other drug (oxazepam or metyrapone) is coated on top of the inert coating, and where also optionally, an inert coating is applied on top of the most exterior drug layer. |
| 8 | Bilayer compressed tablets in which one layer comprises metyrapone and the second layer comprises oxazepam, with an optional outer coating of an inert layer. |

TABLE 1-continued

9. Trilayer compressed tablets in which one layer comprises metyrapone, a second layer (middle layer) comprises an inert material, and a third layer comprises oxazepam, with an optional outer coating of another inert material.
10. Blends of metyrapone combined with beads of oxazepam in capsules; the beads of oxazepam having an outer coating.
11. Blends of oxazepam combined with beads of metyrapone in capsules; the beads of metyrapone having an outer coating.
12. Beads of metyrapone combined with granules of oxazepam in capsules; the beads of metyrapone have an outer coating; and, optionally, the granules of oxazepam are coated.

General compositions of each formulation type are presented below in Table 2. The w/w % ranges are percentages for the complete composition.

TABLE 2

| Component | Formulation | | | | | | | |
|---|---|---|---|---|---|---|---|---|
| | 1 | 2 | 3 | 4/5/10/11/12 | 6 | 7 | 8 | 9 |
| | % w/w (Range) | | | | | | | |
| Active (Metyrapone + Oxazepam) | 1-90 | 1-90 | 1-95 | 1-95 | 1-80 | 1-90 | 1-90 | 1-90 |
| Filler (Solid) | 10-99 | 10-99 | 5-99 | 5-99 | 0-10 | 10-99 | 10-99 | 10-99 |
| Binding agent | 0.05-20 | 0.05-20 | 0.05-20 | 0.0-20 | 0-5 | 0.05-20 | 0.05-20 | 0.05-20 |
| Disintegrating agent | 0.05-20 | 0.05-20 | 0.05-20 | 0.05-20 | 0-5 | 0.05-20 | 0.05-20 | 0.05-20 |
| Glidant | 0.05-2 | 0.05-2 | 0 | 0 | 0 | 0.05-2 | 0.05-2 | 0.05-2 |
| Lubricating agent | 0.1-3 | 0.1-3 | 0 | 0 | 0 | 0.1-3 | 0.1-3 | 0.1-3 |
| Solubilizing agent | 0 | 0 | 0 | 0 | 20-70 | 0 | 0 | 0 |
| Antioxidants | 0-5 | 0-5 | 0-5 | 0-5 | 0-5 | 0-5 | 0-5 | 0-5 |
| Preservatives | 0 | 0 | 0 | 0 | 0-3 | 0 | 0 | 0 |
| Inert Coating which may contain pigments, dyes or inks | 0 | 0.05-10 | 0.05-10 | 0-10 | 0-20 | 0.05-20 | 0-10 | 0-10 |
| Capsule | Yes | Yes | Yes | Yes | Yes[a] | No | No | No |

[a]Capsule is formed during processing, not as a separate component. The filler/binding agent/disintegrant could be in the outer drug coating.

Formulation 1: Minitabs in Capsules

The general composition of the minitabs of formulation 1 are shown below in Table 3.

TABLE 3

| Minitab Ingredient Type | % w/w (Range) |
|---|---|
| Active (Metyrapone or Oxazepam) | 1-90 |
| Filler | 10-99 |
| Binding agent | 0.05-10 |
| Disintegrating agent | 0.05-20 |
| Glidant | 0.05-2 |
| Lubricating agent | 0.1-3 |

Minitabs are then filled into appropriately sized gelatin or HPMC capsules.

The composition of metyrapone minitabs (30 mg drug product) is provided in Table 4.

TABLE 4

| Ingredient | Purpose | mg/minitab | % w/w |
|---|---|---|---|
| Metyrapone drug substance | Active | 30.00 | 50.0 |
| Dibasic calcium phosphate anhydrous, USP | Filler | 21.84 | 36.4 |
| Hydroxypropyl methyl cellulose, NF[a] | Binding agent | 3.36 | 5.6 |
| Croscarmellose sodium, NF | Disintegrating agent | 3.00 | 5.0 |
| Colloidal silicon dioxide, NF | Glidant | 0.60 | 1.0 |
| Magnesium stearate, NF | Lubricating agent | 1.20 | 2.0 |
| Total | | 60.00 | 100.0 |

[a]Hydroxypropyl methyl cellulose, NF, is also referred to as hypromellose, NF.

The manufacturing process for metyrapone minitabs, 30 mg, is summarized in the following steps:

1. Half of the dibasic calcium phosphate, all of the metyrapone, all of the hypromellose, and the other half of the dibasic calcium phosphate are sequentially screened through a 20-mesh screen and then placed into the bowl of a high-shear mixer.
2. The dry ingredients are mixed for 5 minutes with a chopper speed of 4000 rpm and impeller speed of 250 rpm.
3. While mixing is continued with the same chopper and impeller speeds, about 35 g of sterile water for irrigation is added per kg of dry ingredients at a flow rate of 17 g/minute. Mixing is continued for 5 additional minutes.
4. Granules are dried in a fluid bed dryer with an inlet air temperature of 35 to 40° C. until the loss on drying (LOD) is not >1%.
5. The dried granules are passed through a 20-mesh screen.

6. The weights of croscarmellose sodium and colloidal silicon dioxide are adjusted based on the yield of granules, and these ingredients are screened and added to the granules in a V-blender. The ingredients are then blended for 10 minutes.
7. The magnesium stearate is screened and added to the blend, and blending is continued for an additional 3 minutes.
8. The blend is transferred to the hopper of a tablet press fit with 0.125-inch punches, and minitabs are compressed to target weight of 60.0 mg, and a target hardness of 13 kP (range 7 to 19 kP).

The composition of the oxazepam minitabs (4 mg drug product) is provided in Table 5.

TABLE 5

| Ingredient | Purpose | mg/minitab | % w/w |
|---|---|---|---|
| Oxazepam drug substance | Active | 4.00 | 8.0% |
| Lactose anhydrous, NF | Filler | 44.20 | 88.4% |
| Hydroxypropyl cellulose, NF | Binding agent | 0.30 | 0.6% |
| Croscarmellose sodium, NF | Disintegrating agent | 0.50 | 1.0% |
| Colloidal silicon dioxide, NF | Glidant | 0.50 | 1.0% |
| Magnesium stearate, NF | Lubricating agent | 0.50 | 1.0% |

The manufacturing process for oxazepam minitabs (4 mg) is summarized in the following steps:
1. One-fourth (¼) of the lactose, then all of the oxazepam, and then ¼ of the lactose are passed through a 30-mesh screen.
2. The hydroxypropyl cellulose, croscarmellose sodium, and colloidal silicon dioxide are passed through the same screen.
3. The remaining lactose is passed through the same screen.
4. The screened materials are transferred to a suitably sized V-blender and blended for 10 minutes.
5. The magnesium stearate is passed through the same 30-mesh screen used previously and added to the blended ingredients in the V-blender. The components are blended for 3 minutes.
6. The blend is transferred to the hopper of a tablet press fit with 0.125-inch punches, and minitabs are compressed to a target weight of 50.0 mg.

Size AA elongated gelatin capsules were used to encapsulate the metyrapone and oxazepam minitabs for administration to subjects. Each of these capsules can hold a maximum of 12 minitabs. Table 6 describes how many of each type of minitab were placed into each capsule, and how many capsules were required, for each dose level tested.

TABLE 6

| metyrapone dose (mg/oxazepam dose (mg) for admin. BID | metyrapone minitabs per dose | oxazepam minitabs per dose | capsules per dose | metyrapone minitabs per capsule | oxazepam minitabs per capsule | minitabs per capsule |
|---|---|---|---|---|---|---|
| 270/12 | 9 | 3 | 3 | 3 | 1 | 4 |
| 540/24 | 18 | 6 | 3 | 6 | 2 | 8 |
| 720/24 | 24 | 6 | 3 | 8 | 2 | 10 |

Formulation 2: Coated Minitabs in Capsules

Minitabs of the general formulation of Type 1 above, are coated with an inert coating for tablets (e.g., coatings from Colorcon such as an Opadry coating), using either a pan coater, fluid bed dryer or Wurster coater. Coatings can add from 0.05 to 10% to the total weight of the minitabs. Such minitabs may be placed into gelatin or HPMC capsules.

Formulation 3: Beads in Capsules with an Inert Outer Coating

A general composition of beads (from an extrusion spheronization process) is shown in Table 7.

TABLE 7

| Bead Ingredient Type | % w/w (Range) |
|---|---|
| Active (oxazepam or metyrapone) | 1-95 |
| Filler | 5-99 |
| Binding agent | 0.05-20 |
| Disintegrating agent | 0.05-20 |

Beads of the general formulation above may be coated with an inert coating for tablets (e.g., coatings from Colorcon such as an Opadry coating), using either a pan coater, fluid bed dryer or Wurster coater. Coatings can add from 0.05 to 10% to the total weight of the beads. Such beads may be placed into gelatin or HPMC capsules.

Formulation 4: Granules of Metyrapone and Coated Beads of Oxazepam

The blended metyrapone from Formulation 10 was used to produce dry granules of metyrapone. 1200 g of the metyrapone blend was loaded into a roller compactor and ribbons were collected. Approximately 10.0 g samples of the ribbons were collected for in-process testing at the beginning and the end of the run to determine ribbon porosity using Geopyc measurements of absolute and envelope densities. At the end of the process, the compacted material was passed through a 20 mesh screen. The compacted and fine material were collected in separate bags. The ribbons were collected and co-milled. The milled material was transferred to an appropriate size V-shell and blended for 3 minutes at 25 rpm. The resultant granules from the V-blender was unloaded into a PE bag and the weight recorded.

Granules of the formulation may optionally be coated with an inert coating for tablets (e.g., coatings from Colorcon such as an Opadry coating), using either a pan coater, fluid bed dryer or Wurster coater. Coatings can add from 0.05 to 10% to the total weight of the beads.

Granules may also be prepared by wet granulation. Wet granulation: See steps 1-5 of the process for the metyrapone minitabs above. This yielded granules of metyrapone. The composition of metyrapone granules made with a wet granulation process is shown in Table 8.

TABLE 8

| Ingredient | Purpose | g/batch | % w/w |
|---|---|---|---|
| Metyrapone | Active | 500 | 54.3 |
| Dibasic calcium phosphate anhydrous, USP | Filler | 364 | 39.6 |
| Hydroxypropyl methyl cellulose, NF[a] | Binding agent | 56 | 6.1 |

[a]Hydroxypropyl methyl cellulose, NF, is also referred to as hypromellose, NF

Alternative dry granulation: This was performed as part of the process used to evaluate simple combination tablets of metyrapone and oxazepam, with the granules of metyrapone made as part of the process for the single layer combination tablet. The composition of metyrapone granules made with a dry granulation process is shown in Table 9.

TABLE 9

| Ingredient | Purpose | Quantity (g/batch) | % w/w |
|---|---|---|---|
| Metyrapone drug substance | Active | 98.50 | 51.8 |
| Lactose Anhydrous | Filler | 82.08 | 43.1 |
| Hydroxypropyl cellulose | Binding agent | 5.75 | 3.0 |
| Croscarmellose sodium | Disintegrating agent | 4.00 | 2.1 |

The manufacturing process for the alternative dry metyrapone granules is summarized in the following steps:
1. Half of the lactose anhydrous, all of the metyrapone, all of the hydroxypropyl cellulose, all of the croscarmellose sodium, and the other half of the lactose anhydrous are sequentially screened through a 20-mesh screen, and added into a Turbula mixer.
2. The ingredients are mixed for 15 minutes in a Turbula mixer.
3. The resultant blend is roller compacted on a Vector roller compactor, with a DPS roller type, 700 lbs roll force, 3 rpm roller speed, and a roll gap of 2 mm, yielding granules.

Oxazepam beads were prepared with the ingredients listed in Table 10 and the procedure below.
1. Each of the solid ingredients were weighed and screened through a #20 mesh screen and transferred to a high shear mixer granulator bowl.
2. The solid ingredients were blended in the high shear granulator for 5 minutes at 150 rpm (impeller only). After 5 minutes, the LOD for the dry mixture was measured.
3. The granulator impeller speed was set at approximately 250 RPM and the chopper speed at approximately 1000 RPM. Purified water was added at approximately 40 g/minute to the mixture to prepare the granulation. The amount of water, impeller speed and chopper speeds were adjusted as needed to obtain a wet pliable mass.
4. The wet mass was loaded on the LCI MG-55 Multi-Granulator extruder equipped with 1.0 mm size screen (target: 1.0 mm; range: 0.7 mm-1.2 mm).
5. The extrudate was collected and charged to a LCI QJ-230T Marumerizer spheronizer equipped with 2 mm cross hatch disc. The spheronizer speed was adjusted to the desired setting. A portion of the extrudate was added and processed for with regular visual observations/sampling to determine the processing conditions and end point. The time start and time stop for each sub-lot were recorded. Once the time elapsed, the discharge valve was opened and the spheres were collected into an appropriate container.
6. The spherules were transferred into the expansion chamber of the fluid bed dryer. The spherules were dried at an inlet temperature of 60° C. The fluidization conditions used were recorded.
7. The resulting beads were sifted through a nest of screens from #16-#25. The PSD was determined in this range.
8. The beads were then coated with Opadry QX White to a theoretical 7.5% weight gain.

TABLE 10

| Ingredient | Percent (w/w) | mg/dose | Batch Quantity (g) |
|---|---|---|---|
| Oxazepam | 5.71 | 4 | 85.7 |
| Lactose Fastflo 310 | 64.29 | 45 | 964.3 |
| Microcrystalline Cellulose PH 101 | 10 | 7 | 150 |
| Corn Starch | 5 | 3.5 | 75 |
| Polyplasdone XL | 10 | 7 | 150 |
| Povidone K30 | 3 | 2.1 | 45 |
| Sodium lauryl sulfate | 2 | 1.4 | 30 |
| Purified Water[1] | qs | qs | qs |

[1]Evaporated on drying.

HPMC capsules were filled with 148.4 mg of the oxazepam coated beads (containing 8 mg of oxazepam) and 300 mg of the metyrapone granules (containing 240 mg of metyrapone).

Formulation 6: Softgels with an Inner Solution of Metyrapone and an Outer Coating of Oxazepam A softgel composition such as that used for commercial metyrapone softgels containing solubilizing agents (e.g., polyethylene glycol, glycerine) and optionally antioxidants or preservatives, is then coated with an optional inert inner coating (e.g., coatings from Colorcon such as an Opadry coating), using either a pan coater, fluid bed dryer or Wurster coater. Coatings can add from 0.05 to 10% to the total weight of the cores. The coated cores are then coated in a layer with either a solution or suspension containing the oxazepam, using either a pan coater, fluid bed dryer or Wurster coater. Active coatings can add from 0.05 to 20% of the second active to the total weight of the tablet. An optional inert outer coating (e.g., coatings from Colorcon such as an Opadry coating), using either a pan coater, fluid bed dryer or Wurster coater can then be applied. Coatings can add from 0.05 to 10% to the total weight of the cores.

Formulation 7: Multilayer Tablets

A general composition of metyrapone or oxazepam (from an extrusion spheronization process) is shown in Table 11. This serves as the core of the multilayer tablet.

TABLE 11

| Tablet Core Ingredient Type | % w/w (Range) |
|---|---|
| Active (metyrapone or oxazepam) | 1-90 |
| Filler | 10-99 |
| Binding agent | 0.05-20 |
| Disintegrating agent | 0.05-20 |
| Glidant | 0.05-2 |
| Lubricating agent | 0.1-3 |

The cores of the general formulation above are coated with an inert coating for tablets (e.g., coatings from Colorcon such as an Opadry coating), using either a pan coater, fluid bed dryer or Wurster coater. Coatings can add from 0.05 to 10% to the total weight of the cores. The coated cores are then coated in a layer with either a solution or suspension containing the second active (second drug), using either a pan coater, fluid bed dryer or Wurster coater. Active coatings can add from 0.05 to 20% of the second active to the total weight of the tablet. The multilayer tablets are optionally coated with an inert coating for tablets (e.g., coatings from Colorcon such as an Opadry coating), using either a pan coater, fluid bed dryer or Wurster coater. Inert coatings can add from 0.05 to 10% to the total weight of the tablet.

Formulation 8: Bilayer Compressed Tablets

A general composition of active layer is shown in Table 12.

TABLE 12

| Active Layer Ingredient Type | % w/w (Range) |
| --- | --- |
| Active (metyrapone or oxazepam) | 1-90 |
| Filler | 10-99 |
| Binding agent | 0.05-20 |
| Disintegrating agent | 0.05-20 |
| Glidant | 0.05-2 |
| Lubricating agent | 0.1-3 |

Blends of the ingredients (which can be in the form of granules) are made separately for metyrapone and oxazepam as actives. Using a bilayer tablet press, such blends are used to produce a bilayer tablet where metyrapone and oxazepam are in limited or no contact with each other. The bilayer tablets are optionally coated with an inert coating for tablets (e.g., coatings from Colorcon such as an Opadry coating), using either a pan coater, fluid bed dryer or Wurster coater. Inert coatings can add from 0.05 to 10% to the total weight of the tablet Formulation 9: Trilayer Compressed Tablets Blends of the ingredients as described for the bilayer tablets (which can be in the form of granules) are made separately for metyrapone and oxazepam as actives. A general composition of an inert middle layer is shown in Table 13.

TABLE 13

| Inert Middle Layer Ingredient Type | % w/w (Range) |
| --- | --- |
| Filler | 65-100 |
| Binding agent | 0.05-20 |
| Disintegrating agent | 0.05-20 |
| Glidant | 0.05-2 |
| Lubricating agent | 0.1-3 |

Using a trilayer tablet press these blends can produce a trilayer tablet where metyrapone and oxazepam are separated by the inert middle layer. The trilayer tablets are optionally coated with an inert coating for tablets (e.g., coatings from Colorcon such as an Opadry coating), using either a pan coater, fluid bed dryer or Wurster coater. Inert coatings can add from 0.05 to 10% to the total weight of the tablet.

Formulation 10. Blend of Metyrapone Combined with Beads of Oxazepam in Capsules

A dry blend of metyrapone was prepared with the ingredients listed in Table 14. The metyrapone was weighed and passed through a #20 mesh screen. The microcrystalline cellulose and colloidal silicon dioxide were combined, mixed in a polybag, and passed through a #20 mesh screen. The metyrapone, microcrystalline cellulose, and colloidal silicon dioxide were blended in a 8 qt. V-Blender for 10 minutes (25 RPM). The magnesium stearate was weighed and passed through a 40 mesh screen, which was then added to the V-Blender, and the mixture was blended for 3 minutes to obtain the final blend.

TABLE 14

| Ingredient | Manufacturer | % w/w | mg/ Capsule | Batch Quantity (g) |
| --- | --- | --- | --- | --- |
| Metyrapone | | 80.0 | 240.0 | 1600 |
| Microcrystalline cellulose (Avicel PH 102) | FMC Biopolymer | 18.5 | 55.5 | 370 |
| Colloidal silicon dioxide (Cab-O-Sil) | CABOT | 1 | 3.0 | 20 |
| Magnesium stearate, NF (Hyqual- Non bovine | Mallickrodt/ Covidien | 0.5 | 1.5 | 10 |
| Total Weight | | | 300.0 | 2000 |

Oxazepam beads were prepared with the ingredients listed in Table 15 and the procedure below.

1. Each of the solid ingredients were weighed and screened through a #20 mesh screen and transferred to a high shear mixer granulator bowl.

2. 180 g of purified water was mixed with the Povidone K30 with an overhead mixer creating the binder solution.

3. The solid ingredients were blended in the high shear granulator for 5 minutes at 150 rpm (impeller only). After 5 minutes, the LOD for the dry mixture was measured.

4. The granulator impeller speed was set at approximately 250 RPM and the chopper speed at approximately 750 RPM. The binder solution was added at approximately 100 g/minute.

Additional purified water was added at approximately 60-100 g/minute to the mixture to to obtain a wet pliable mass (the wet granule mass), with the impleller speed set to approximately 250-350 rpm, and the chopper speed set to 750 rpm. Approximately 222 g of water was added.

5. The wet granule was mixed for approximately 1.5 minutes with the granulator impeller speed at approximately 350 RPM and the chopper at approximately 1000 RPM.

6. The wet mass was loaded on the LCI MG-55 Multi-Granulator extruder equipped with 1.0 mm size screen (target: 1.0 mm; range: 0.7 mm-1.2 mm).

7. The extrudate was collected and charged to a LCI QJ-230T Marumerizer spheronizer equipped with 2 mm cross hatch disc. The spheronizer speed was adjusted to the desired setting. A portion of the extrudate was added and processed for approximately 2 minutes with regular visual observations/sampling to determine the processing conditions and end point. The time start and time stop for each sub-lot were recorded. Once the time elapsed, the discharge valve was opened and the spheres were collected into an appropriate container.

8. The spherules were transferred into the expansion chamber of the fluid bed dryer. The spherules were dried at an inlet temperature of 60° C. and product temperature 35-40° C. to obtain a LOD within ±1.0 of the value obtained in step 3. The fluidization conditions used were recorded. Also, the final weight of spherules obtained was recorded. If the temperature exceeded 40° C., the process was discontinued until further optimization.

9. The resulting beads were sifted through a nest of screens, with beads collected on screens #18-#25 combined.

10. The beads were then coated with Opadry QX White to a nominal 7.5% weight gain.

TABLE 15

| Ingredient | Percent (w/w) | mg/dose | Batch Quantity (g) |
|---|---|---|---|
| Oxazepam | 5.71 | 4 | 85.7 |
| Lactose Fastflo 310 | 64.79 | 45.35 | 971.8 |
| Microcrystalline Cellulose PH 101 | 15 | 10.5 | 225.0 |
| Polyplasdone XL | 10 | 7 | 150.1 |
| Povidone K30 | 3 | 2.1 | 45.0 |
| Sodium lauryl sulfate | 1.5 | 1.05 | 22.5 |
| Purified Water[1] | qs | qs | qs |

[1]Evaporated on drying.

HPMC capsules were 149.1 mg of the oxazepam coated beads (containing 8 mg of oxazepam) and 300 mg of the metyrapone dry blend (containing 240 mg of metyrapone)..
Formulation 11. Blend of Metyrapone Combined with Beads of Oxazepam in Capsules A dry blend of metyrapone was prepared with the ingredients listed in Table 14B. The metyrapone was weighed and passed through a #20 mesh screen. The microcrystalline cellulose was weighed and passed through a #20 mesh screen. A portion of the microcrystalline cellulose and the colloidal silicon dioxide were combined, mixed in a polybag, and passed through a #40 mesh screen. The metyrapone, microcrystalline cellulose, and colloidal silicon dioxide were blended in a 16 qt. V-Blender for 12 minutes (25 RPM). The magnesium stearate was weighed and passed through a #40 mesh screen, and was then added to the V-Blender, and the mixture was blended for 3 minutes to obtain the final blend.

TABLE 14B

| Ingredient | Manufacturer | % w/w | Batch Quantity (g) |
|---|---|---|---|
| Metyrapone | | 80.0 | 3600.2 |
| Microcrystalline cellulose (Avicel PH102) | FMC Biopolymer | 18.5 | 832.5 |
| Colloidal silicon dioxide (Cab-O-Sil) | CABOT | 1 | 45.07 |
| Magnesium stearate, NF (Hyqual-Non bovine | Mallickrodt/ Covidien | 0.5 | 22.53 |

Oxazepam beads were prepared with the ingredients listed in Table 15B and the procedure below.

1. Each of the solid ingredients except for Povidone K30 were weighed and screened through a #20 mesh screen and transferred to a high shear mixer granulator bowl.

2. 180 g of purified water was mixed with the Povidone K30 with an overhead mixer creating the binder solution.

3. The solid ingredients were blended in the high shear granulator for 5 minutes at 150 rpm (impeller only). After 5 minutes, the LOD for the dry mixture was measured.

4. The granulator impeller speed was set at approximately 250 RPM and the chopper speed at approximately 750 RPM. The binder solution was added at approximately 100 g/minute.

5. Additional purified water was added at approximately 60-100 g/minute to the mixture to obtain a wet pliable mass (the wet granule mass), with the impleller speed set to approximately 250-350 rpm, and the chopper speed set to 750 rpm. Approximately 222 g of water was added.

6. The wet granule mass was mixed for approximately 1.5 minutes with the granulator impeller speed at approximately 350 RPM and the chopper at approximately 1000 RPM.

7. The wet mass was loaded on the LCI MG-55 Multi-Granulator extruder equipped with 1.0 mm size screen (target: 1.0 mm; range: 0.7 mm-1.2 mm).

8. The extrudate was collected and charged to a LCI QJ-230T Marumerizer spheronizer equipped with 2 mm cross hatch disc. The spheronizer speed was adjusted to the desired setting. A portion of the extrudate was added and processed for approximately 2 minutes with regular visual observations/sampling to determine the processing conditions and end point. The time start and time stop for each sub-lot were recorded. Once the time elapsed, the discharge valve was opened and the spheres were collected into an appropriate container.

9. The spherules were transferred into the expansion chamber of the fluid bed dryer. The spherules were dried at an inlet temperature of 60° C. and product temperature 35-40° C. to obtain a LOD within ±1.0 of the value obtained in step 3. The fluidization conditions used were recorded. Also, the final weight of spherules obtained was recorded. If the temperature exceeded 40° C., the process was discontinued until further optimization.

10. The resulting beads were sifted through a nest of screens, with beads collected on screens #18-#25 combined..

11. The resultant beads were then coated in portions with a 15% dispersion of Opadry QX White in water in a fluid bed dryer equipt with a Wurster column to a nominal 7.5% weight gain on the uncoated beads (7.0% of the total weight total of the coated beads). An example of batch amounts for one of the coating portions is shown in Table 15C.

12. Coated bead portions were blended in a bag.

TABLE 15B

| Ingredient | Batch Quantity (g) Uncoated Beads | Percent (w/w) Uncoated Beads |
|---|---|---|
| Oxazepam | 85.7 | 5.71 |
| Lactose Monohydrate Fastflo 310 | 971.8 | 64.79 |
| Microcrystalline Cellulose PH 101 | 225.0 | 15 |
| Polyplasdone XL (Crospovidone) | 150.1 | 10 |
| Povidone K30 | 45.0 | 3 |
| Sodium lauryl sulfate | 22.5 | 1.5 |
| Purified Water[1] | qs | qs |

[1]Evaporated on drying.

TABLE 15C

| Ingredient | Batch Quantity (g) Coated Beads | Percent (w/w) Coated Beads |
|---|---|---|
| Uncoated Oxazepam Beads | 296.2 | 93 |
| Opadry QX White[2] | 22.49 | 7 |
| Purified Water[1] | qs | qs |

[1]Evaporated on drying.
[2]Opadry QX White (22.49 g) was spray coated onto the uncoated oxazepam beads as 149.9 g of a 15% w/w dispersion in water.

HPMC capsules were filled with the combination of 8 mg of oxazepam per capsule in the form of the coated oxazepam beads and 240 mg of metyrapone per capsule in the form of the metyrapone dry blend. HPMC capsules were filled with the combination of 4 mg of oxazepam per capsule in the form of the coated oxazepam beads and 90 mg of metyrapone per capsule in the form of the metyrapone dry blend. The composition of the capsule fills is shown in Table 15D.

TABLE 15D

Composition of Capsule Fills

| Ingredient | mg/capsule (90 mg and 4 mg combination) | mg/capsule (240 mg and 8 mg combination) |
|---|---|---|
| Metyrapone | 90.0 | 240.0 |
| Oxazepam | 4.0 | 8.0 |
| Microcrystalline cellulose PH-102 | 20.8 | 55.5 |
| Microcrystalline cellulose PH-101 | 10.5 | 21.0 |
| Lactose monohydrate | 45.4 | 90.7 |
| Colloidal silicon dioxide | 1.1 | 3.0 |
| Magnesium stearate | 0.6 | 1.5 |
| Polyplasdone XL (Crospovidone) | 7.0 | 14.0 |
| Povidone K30 | 2.1 | 4.2 |
| Sodium Lauryl Sulfate | 1.1 | 2.1 |
| Opadry QX White | 5.3 | 10.5 |
| Total Capsule Fill | 187.9 | 450.5 |

Metyrapone-Oxazepam Compatibility Study

A study was conducted to assess the compatibility between oxazepam and metyrapone in a single pharmaceutical composition (e.g., single tablet unit containing both compounds).

Analytical Methods Assessment

Stressed oxazepam and metyrapone drug substance samples were created and analyzed using the HPLC assay and related substances method for each compound. This assessed whether impurities from oxazepam interfere with impurities from metyrapone or metyrapone itself and vice versa when analyzed using each method.

Compatibility Testing

Binary mixtures of the drug substances were prepared, stressed at 40° C./75% RH for 4 weeks and evaluated by the assay and related substances method using both analytical methods. Prototype blends containing oxazepam and metyrapone were prepared that would represent potential approaches for a single unit combination tablet with (i) one prototype using dry granulation and (ii) one prototype using wet granulation. The blends were stressed at 25° C./60% RH and at 40° C./75% RH for 4 weeks and evaluated.

Analytical Methods Assessment

Forced degraded samples of oxazepam and metyrapone drug substances were analyzed by each of the following methods.

Test Method A

Accurately weigh samples into a volumetric flask. Add approximately 2 mL of water to disintegrate the samples. Add sample diluent, sonicate for 15 minutes, shake for 15 minutes, and then bring to volume with sample diluent and mix well. Filter the solution, dilute as needed with the sample diluent for analysis, and analyze by HPLC using the chromatographic conditions below.

Chromatographic Conditions Developed for Oxazepam

| Column | Zorbax SB-C18, 150 × 4.6 mm, 3.5 μm, or equivalent |
|---|---|
| Column temperature | Room temperature |
| Detector | Ultraviolet, 232 nm |
| Flow rate | 1.0 mL/min |
| Mobile phase | 62 mM $K_2HPO_4$ buffer, pH 6.5 |
| Mobile Phase B | Methanol |

| Time (minutes) | Mobile Phase A | Mobile Phase B |
|---|---|---|
| Gradient 0 | 60% | 40% |
| 30 | 60% | 40% |
| 50 | 40% | 60% |
| 65 | 40% | 60% |
| 65.1 | 60% | 40% |
| 75 | 60% | 40% |

| Sample diluent | 10:90 Water:Methanol |
|---|---|
| Injection volume | 20 μL |

Test Method B

Accurately weigh samples into a 500 mL volumetric flask. Add approximately 1 to 2 mL of water to disintegrate. Add sample diluent, sonicate for 15 minutes, shake for 15 minutes, and then bring to volume with sample diluent and mix well. Filter this solution and dilute to an appropriate sample concentration with sample diluent, and analyze by HPLC using the chromatographic conditions below.

Chromatographic Conditions Developed for Metyrapone

| Column | ACE C18, 150 × 4.6 mm, 5 μm, or equivalent |
|---|---|
| Column temperature | 30° C. |
| Detector | Ultraviolet, 232 nm |
| Flow Rate | 1.5 mL/min |
| Mobile Phase A | 25 mM $K_2HPO_4$ buffer, pH 6.5 |
| Mobile Phase B | Methanol |

| Time (minutes) | Mobile Phase A | Mobile Phase B |
|---|---|---|
| Gradient 0 | 85% | 15% |
| 25 | 50% | 50% |
| 32 | 30% | 70% |
| 34 | 30% | 70% |
| 35 | 85% | 15% |
| 40 | 85% | 15% |

| Sample diluent | Water/acetonitrile 1:1 |
|---|---|

Compatibility Study

The compatibility between the two compounds was evaluated as (i) neat API mixtures (1:15 and 1:30 ratios of oxazepam:metyrapone) and (ii) in prototype matrices that are representative of final forms if a simple combination tablet were to be manufactured (see Table 16). These prototypes have metyrapone and oxazepam ratios representative of a 720 mg metyrapone/24 mg oxazepam dose.

One prototype was prepared using a dry granulation process while the other was prepared using a wet granulation process. In both prototypes, metyrapone was formulated intragranularly while oxazepam included extragranularly. The excipients used in each case were similar to those used on oxazepam and metyrapone minitabs formulations. The dry granulation process was facilitated through roller compaction of the intragranular components.

TABLE 16

| Prototype | Composition | Rationale |
|---|---|---|
| 1 | Intragranular:<br>Metyrapone 49.25%<br>Lactose anhydrous 41.04%<br>HPC 2.87%<br>Croscarmellose sodium 2.00%<br>Extragranular:<br>Oxazepam 1.64%<br>Croscarmellose sodium 1.76%<br>MCC<br>Colloidal silica 0.48%<br>Magnesium stearate 0.96% | To assess the compatibility between metyrapone and oxazepam in a potential dry granulation process using excipients that have been previously shown to be compatible with the two active compounds. |
| 2 | Intragranular:<br>Metyrapone 49.25%<br>Lactose anhydrous 41.04%<br>HPMC 2.87%<br>Croscarmellose sodium 2.00%<br>Water QS<br>Extragranular:<br>Oxazepam 1.64%<br>Croscarmellose sodium 1.76%<br>MCC<br>Colloidal silica 0.48%<br>Magnesium stearate 0.96% | To assess the compatibility between metyrapone and oxazepam in a potential wet granulation process using excipients that have been previously shown to be compatible with the two active compounds. |

Samples of API mixtures and prototype tablets (created from slugs compressed on a Carver press) were stored at 25° C./60% RH and at 40° C./75% RH in glass vials with screw caps. Samples were removed from storage after 4 weeks and analyzed for metyrapone, oxazepam and related substances using both HPLS analytical methods (Test methods A and B). Different dilutions were required to appropriately analyze for metyrapone and oxazepam from the mixtures due to the large amount of metyrapone relative to oxazepam.

Results—Compatibility Study

The compatibility of metyrapone and oxazepam was evaluated by comparing potency and impurity profiles of the following samples:
1. Neat oxazepam API stored for 4 weeks at 25° C./60% RH and 40° C./75% RH.
2. Neat metyrapone API stored for 4 weeks at 25° C./60% RH and 40° C./75% RH.
3. Binary mixtures of oxazepam and metyrapone APIs at 1:15 and 1:30 ratios stored for 4 weeks at 25° C./60% RH and 40° C./75% RH.
4. Prototype blend prepared using the wet granulation approach (metyrapone—intragranular; oxazepam—extragranular) stored for 4 weeks at 25° C./60% RH and 40° C./75% RH.
5. Prototype blend prepared using the dry granulation approach (roller compacted metyrapone—intragranular; oxazepam—extragranular) stored for 4 weeks at 25° C./60% RH and 40° C./75% RH.

For each active pharmaceutical component, the potency and impurity values of neat API were compared with those for the binary mixtures and prototypes. Since the methods are unable to distinguish impurities from the two actives, compatibility was assessed by the increase in total impurities and decrease in potency values of the actives. The results are shown in Table 17 for oxazepam and Table 18 for metyrapone. The % peak areas for API admixtures and prototypes are proportional to the ratio of the two actives in the corresponding samples.

The results collectively demonstrate the incompatibility between the two actives. The severity of incompatibility follows dry granulation <wet granulation <admixtures. As expected, degradation is greater at 40° C./75% RH than at 25° C./60% RH. The neat APIs show no degradation in the same duration of storage as the admixtures and prototypes even at 40° C./75% RH. The incompatibility resulted primarily in degradation of oxazepam (up to 50% oxazepam degradation was observed in 4 weeks at 40° C./75% RH), while the impact on metyrapone, if any, is minimal. In addition, separation of the actives through a granulation approach (metyrapone—intragranular; oxazepam—extragranular) did not have a significant impact on the incompatibility.

TABLE 17

Oxazepam Assay and Related Substances after 4 Weeks of Storage

| | % Peak area values for actives and impurities | | | | | | | | | |
|---|---|---|---|---|---|---|---|---|---|---|
| | oxazepam neat API | | oxazepam in 1:15 API mixture | | oxazepam in 1:30 API mixture | | Wet Granulation | | Dry Granulation | |
| RRT | 25 C. | 40 C. | 25 C. | 40 C. | 25 C. | 40 C. | 25 C. | 40 C. | 25 C. | 40 C. |
| 0.14 | ND | ND | ND | ND | ND | ND | 0.05 | 0.06 | 0.05 | 0.05 |
| 0.25 | ND | ND | ND | ND | ND | ND | 0.08 | 0.08 | 0.08 | 0.07 |
| 0.34 * | ND | ND | 79.17 | 80.71 | 87.75 | 87.24 | 89.59 | 91.13 | 88.44 | 88.11 |
| 0.53 | ND | ND | ND | 0.38 | ND | ND | ND | ND | ND | ND |
| 0.57 | ND | ND | 0.17 | 2.49 | 0.11 | 0.75 | ND | ND | ND | ND |
| 0.58 | ND | ND | ND | ND | ND | 0.21 | ND | ND | ND | ND |
| 0.62 | ND | ND | 0.14 | 2.58 | 0.09 | 0.82 | ND | 0.05 | ND | 0.05 |

TABLE 17-continued

Oxazepam Assay and Related Substances after 4 Weeks of Storage

% Peak area values for actives and impurities

| RRT | oxazepam neat API | | oxazepam in 1:15 API mixture | | oxazepam in 1:30 API mixture | | Wet Granulation | | Dry Granulation | |
|---|---|---|---|---|---|---|---|---|---|---|
| | 25 C. | 40 C. | 25 C. | 40 C. | 25 C. | 40 C. | 25 C. | 40 C. | 25 C. | 40 C. |
| 0.71 | ND | ND | ND | ND | ND | ND | 0.04 | 0.06 | 0.04 | 0.04 |
| 1.00 ** | 99.45 | 99.67 | 20.27 | 12.76 | 11.86 | 10.61 | 10.1 | 6.3 | 11.27 | 10.79 |
| 1.17 | ND | ND | ND | 0.27 | ND | 0.05 | ND | ND | ND | ND |
| 1.28 | 0.25 | 0.15 | ND | ND | ND | ND | 0.02 | 0.02 | 0.03 | 0.02 |
| 1.329 | ND | 0.05 | ND | 0.36 | ND | ND | ND | ND | ND | ND |
| 1.333 | 0.16 | 0.08 | 0.18 | 0.16 | 0.12 | 0.11 | 0.08 | 2.24 | 0.05 | 0.83 |
| 1.58 | ND | ND | ND | 0.06 | ND | 0.11 | ND | ND | ND | ND |
| Total imps at 1 mo | 0.41% | 0.28% | 0.49% | 6.30% | 0.32% | 2.05% | 0.21% | 2.49% | 0.18% | 1.00% |
| Total imps at T0 | | | | | | | 0.20% | | 0.13% | |
| Assay at 1 mo | 95.00% | 93.20% | 103.0% | 66.90% | 102.20% | 86.60% | 85.20% | 52.90% | 97.60% | 93.40% |
| Assay at T0 | | | | | | | 88.60% | | 100.80% | |

\* Metyrapone
\*\* Oxazepam

TABLE 18

Metyrapone Assay and Related Substances after 4 Weeks of Storage

% Peak area values for actives and impurities

| RRT | metyrapone neat | | metyrapone in 1:15 API mixture | | metyrapone in 1:30 API mixture | | Wet Granulation | | Dry Granulation | |
|---|---|---|---|---|---|---|---|---|---|---|
| | 25 C. | 40 C. | 25 C. | 40 C. | 25 C. | 40 C. | 25 C. | 40 C. | 25 C. | 40 C. |
| 0.27 | 0.14 | 0.15 | ND | 0.07 | ND | 0.05 | 0.02 | 0.01 | 0.01 | 0.01 |
| 0.48 | 0.05 | 0.06 | ND | 0.06 | ND | ND | ND | ND | ND | ND |
| 0.67 | 0.01 | ND | ND | ND | ND | ND | 0.05 | 0.05 | 0.05 | 0.04 |
| 0.82 | ND | ND | ND | ND | ND | ND | 0.08 | 0.09 | 0.09 | 0.08 |
| 1.00 * | 99.44 | 99.42 | 79.33 | 80.89 | 88.91 | 88.67 | 88.45 | 90.81 | 89.03 | 89.19 |
| 1.09 | 0.07 | 0.09 | ND | 0.1 | ND | ND | 0.04 | 0.04 | 0.04 | 0.04 |
| 1.4 | ND | ND | 0.17 | 5.13 | 0.12 | 1.39 | ND | 0.09 | ND | 0.12 |
| 1.51** | ND | ND | 20.21 | 12.56 | 10.62 | 9.39 | 11.09 | 6.55 | 10.5 | 9.62 |
| 1.56 | ND | ND | ND | 0.16 | ND | ND | ND | ND | ND | ND |
| 1.68 | ND | ND | ND | 0.35 | ND | ND | ND | ND | ND | ND |
| 1.71 | ND | ND | ND | ND | ND | ND | 0.03 | 2.04 | ND | 0.6 |
| Total imps at 1 mo | 0.26% | 0.30% | 0.17% | 5.97% | 0.12% | 1.54% | 0.13% | 2.27% | 0.14% | 0.80% |
| Total imps at T0 | | | | | | | 0.08% | | 0.08% | |
| Assay at 1 mo | 100.60% | 99.50% | 100.30% | 98.80% | 99.80% | 100.00% | 98.40% | 98.60% | 98.60% | 97.80% |
| Assay at T0 | | | | | | | 96.30% | | 99.40% | |

\* Metyrapone
\*\*Oxazepam

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A capsule or tablet comprising
   metyrapone or a pharmaceutically acceptable salt thereof; and
   oxazepam or a pharmaceutically acceptable salt thereof;
   wherein said metyrapone or a pharmaceutically acceptable salt thereof and said oxazepam or a pharmaceutically acceptable salt thereof are not in physical contact with each other.

2. The capsule or tablet of claim 1 comprising about 5 mg to about 1500 mg of said metyrapone or a pharmaceutically acceptable salt thereof, and/or 2 mg to 60 mg of said oxazepam or a pharmaceutically acceptable salt thereof.

3. The capsule or tablet of claim 1, wherein a ratio, by weight, of said metyrapone or a pharmaceutically acceptable salt thereof to said oxazepam or a pharmaceutically acceptable salt thereof is about 5:1 to about 50:1.

4. The capsule or tablet of claim 1 comprising, by weight, about 20% to about 90% of said metyrapone or a pharmaceutically acceptable salt thereof, and about 0.1% to about 20% of said oxazepam or a pharmaceutically acceptable salt thereof.

5. A method of treating addiction to a substance, the method comprising orally administering to a patient in need thereof the capsule or tablet of claim 1.

6. The capsule or tablet of claim 1, wherein said oxazepam or the pharmaceutically acceptable salt thereof is in a form of a bead.

7. The capsule of claim 6, wherein a diameter of the bead is less than or equal to 2 mm.

8. The capsule or tablet of claim 1, wherein said metyrapone or a pharmaceutically acceptable salt thereof is in a form of a dry blend with at least one pharmaceutically acceptable excipient.

* * * * *